(12) United States Patent
Gao et al.

(10) Patent No.: US 9,809,632 B2
(45) Date of Patent: Nov. 7, 2017

(54) UNIVERSAL PROTEIN TAG FOR DOUBLE STRANDED NUCLEIC ACID DELIVERY

(71) Applicant: UNIVERSITY OF WASHINGTON THROUGH ITS CENTER FOR COMMERCIALIZATION, Seattle, WA (US)

(72) Inventors: Xiaohu Gao, Seattle, WA (US); Hong Yan Liu, Seattle, WA (US)

(73) Assignee: University of Washington Through its Center for Commercialization, Seattle, WA (US)

( * ) Notice: Subject to any disclaimer, the term of this patent is extended or adjusted under 35 U.S.C. 154(b) by 0 days.

(21) Appl. No.: 14/914,922

(22) PCT Filed: Oct. 22, 2014

(86) PCT No.: PCT/US2014/061714
§ 371 (c)(1),
(2) Date: Feb. 26, 2016

(87) PCT Pub. No.: WO2015/061409
PCT Pub. Date: Apr. 30, 2015

(65) Prior Publication Data
US 2016/0222072 A1 Aug. 4, 2016

Related U.S. Application Data

(60) Provisional application No. 61/894,806, filed on Oct. 23, 2013.

(51) Int. Cl.
*C07K 14/47* (2006.01)
*A61K 38/17* (2006.01)
*A61K 31/713* (2006.01)
*C12N 15/11* (2006.01)
*C12N 15/87* (2006.01)

(52) U.S. Cl.
CPC ............ *C07K 14/47* (2013.01); *A61K 31/713* (2013.01); *A61K 38/1709* (2013.01); *C07K 14/4703* (2013.01); *C12N 15/111* (2013.01); *C12N 15/87* (2013.01); *C07K 2319/21* (2013.01); *C07K 2319/80* (2013.01); *C07K 2319/85* (2013.01); *C12N 2310/14* (2013.01); *C12N 2310/16* (2013.01); *C12N 2310/3519* (2013.01); *C12N 2320/32* (2013.01)

(58) Field of Classification Search
CPC ............... C07K 14/47; C07K 2319/21; C07K 2319/80; C07K 14/4703; C07K 2319/85; C12N 15/111; C12N 15/87; C12N 2310/14; C12N 2310/16; C12N 2320/32; C12N 2310/3519; A61K 31/713; A61K 38/1709
See application file for complete search history.

(56) References Cited

U.S. PATENT DOCUMENTS

| 7,772,201 B2 | 8/2010 | Mixson et al. | |
|---|---|---|---|
| 8,273,867 B2 | 9/2012 | Dowdy et al. | |
| 2012/0064599 A1* | 3/2012 | Jayasinghe | ............ C07K 14/31 435/188 |
| 2012/0101045 A1* | 4/2012 | Dowdy | .................. C07K 14/47 514/19.3 |
| 2013/0102654 A1 | 4/2013 | Rossi et al. | |

FOREIGN PATENT DOCUMENTS

| CN | 102349995 A | * | 2/2012 | ............ A61K 38/48 |
|---|---|---|---|---|
| WO | 2010120385 A1 | | 10/2010 | |
| WO | 2010129023 A9 | | 11/2010 | |
| WO | 2010129853 A2 | | 11/2010 | |
| WO | WO 2011/040971 A2 | * | 4/2011 | ........... C12N 9/1252 |
| WO | 2011154331 A1 | | 12/2011 | |
| WO | 2011163121 A1 | | 12/2011 | |
| WO | 2012094653 A2 | | 7/2012 | |

OTHER PUBLICATIONS

Machine translation of CN 102349995 A, pp. 1-30, accessed Feb. 15, 2017.*
Ni-NTA Agarose from Qiagen, from http://www.biocompare.com/Product-Reviews/40836-Ni-NTA-Agarose-From-Qiagen/, Mar. 27, 2007, pp. 1-2.*
PET-32 Vector, from Novagen, Dec. 1998, pp. 1-2.*
Alexis, et al., "Factors Affecting the Clearance and Biodistribution of Polymeric Nanoparticles," Mol. Pharm., vol. 5, pp. 505-515, 2008.
Bagalkot, et al., "siRNA aptamer chimeras on nanoparticles: preserving targeting functionality for effective gene silencing," ACS Nano, vol. 5, pp. 8131-8139, 2011.
Behr, "The proton sponge: A trick to enter cells the viruses did not exploit," Chimia, vol. 51, pp. 34-36, 1997.
Bevilacqua, et al., "Minor groove recognition of double stranded RNA by the double stranded RNA binding domain from the RNA activated protein kinase PKR," Biochem., vol. 35, pp. 9983-9994, 1996.
Bitko, et al., "Inhibition of respiratory viruses by nasally administered siRNA," Nat. Med., vol. 11, pp. 50-55, 2005.
Cabral, et al., "Accumulation of sub 100 nm polymeric micelles in poorly permeable tumours depends on size," Nat. Nanotechnol., vol. 6, pp. 815 823, 2011.
Chang, et al., "Metastatic renal cell carcinoma neovasculature expresses prostate specific membrane antigen," Urology, vol. 57, pp. 801-805, 2001.

(Continued)

*Primary Examiner* — Julie Ha
*Assistant Examiner* — Li Ni Komatsu
(74) *Attorney, Agent, or Firm* — McDonnell Boehnen Hulbert & Berghoff LLP

(57) ABSTRACT

Disclosed herein are chimeric proteins that include one or more double stranded nucleic acid binding domains (dsNABD) and one or more polyHis domains, and compositions that further include a therapeutic double stranded nucleic acid and a targeting ligand bound to the therapeutic double stranded nucleic acid, wherein the dsNABD of the chimeric protein is bound to the therapeutic double stranded nucleic acid, and uses of the compositions to treat disease.

12 Claims, 5 Drawing Sheets

(56) References Cited

OTHER PUBLICATIONS

Chiu, Y.L., et al., "Visualizing a correlation between siRNA localization, cellular uptake, and RNAi in living cells," Chem. Biol., vol. 11, pp. 1165-1175, 2004.
Dassie, et al., "Systemic administration of optimized aptamer siRNA chimeras promotes regression of PSMA expressing tumors," Nat. Biotechnol., vol. 27, pp. 839-849, 2009.
Davis, "The first targeted delivery of siRNA in humans via a self assembling, cyclodextrin polymer based nanoparticle: from concept to clinic," Mol. Pharm., vol. 6, pp. 659-668, 2009.
Derfus, et al., "Targeted quantum dot conjugates for siRNA delivery," Vol Bioconjug. Chem, No. 18, pp. 1391-1396, 2007.
DeVincenzo, et al., "Evaluation of the safety, tolerability and pharmacokinetics of ALN RSV01, a novel RNAi antiviral therapeutic directed against respiratory syncytial virus (RSV)," Antiviral Res., vol. 77, pp. 225-231, 2008.
Dykxhoom, et al., "Killing the messenger: short RNAs that's ilence gene expression," Nat. Rev. Mol. Cell Biol. vol. 4, pp. 457-467, 2003.
Eguchi, et al., "Efficient siRNA delivery into primary cells by a peptide transduction domain dsRNA binding domain fusion protein," Nat. Biotechnol., vol. 27, No. 567, pp. U110, 2009.
Elbakry, A. et al. Layer by layer assembled gold nanoparticles for siRNA delivery. Nano Lett, vol. 9, pp. 2059-2064, 2009.
Green, et al., "2 RNA Binding motifs in the double stranded RNA activated protein kinase, DAI," Genes Dev, vol. 6, pp. 2478-2490, 1992.
Green, et al., "Electrostatic Ligand Coatings of Nanoparticles Enable Ligand Specific Gene Delivery to Human Primary Cells," Nano Lett. vol. 7, pp. 874-879, 2007.
Hannon, G.J. "RNA interference," Nature, vol. 418, pp. 244-251, 2002.
Haussecker, The Business of RNAi Therapeutics in 2012 Molecular Therapy-Nucleic Acids 2, e8; doi:10.1038/mtna.2011.9., downloaded from the Internet at http://www.nature.com/mtna/journal/v1/n2/pdf/mtna20119a.pdf, 2012.
Howard, et al., "RNA interference in vitro and in vivo using a novel chitosan/siRNA nanoparticle system," Mol. Ther., vol. 14, pp. 476-484, 2006.
Jeong, et al., "siRNA conjugate delivery systems," Bioconjug. Chem., vol. 20, pp. 514, 2009.
Kim, et al., "Intracellular small interfering RNA delivery using genetically engineered double-stranded RNA binding protein domain," The Journal of Gene Medicine, vol. 11, No. 9, 2009.
Kim, et al., "Specific recognition of HIV TAR RNA by the dsRNA binding domains (dsRBD1 dsRBD2) of PKR," J. Mol. Biol., vol. 358, pp. 430-442, 2006.
Ko, et al., "Papahadjopoulos Sternberg, B. & Torchilin, V.P. Self assembling micelle like nanoparticles based on phospholipid polyethyleneimine conjugates for systemic gene delivery," J. Controlled Release, vol. 133, pp. 132-138, 2009.
Levy Nissenbaum, et al., "Nanotechnology and aptamers: applications in drug delivery," Trends Biotechnol., vol. 26, pp. 442-449, 2008.
Li, et al., "Using siRNA in prophylactic and therapeutic regimens against SARS coronavirus in rhesus macaque," Nat. Med., vol. 11, pp. 944-951, 2005.
Liu, et al., "A Universal Protein Tag for Delivery of SiRNA-Aptamer Chimeras,", vol. 3, No. 7 XP055166810, 2013.
Liu, et al., "The influence of polymeric properties on chitosan/siRNA nanoparticle formulation and gene silencing," Biomaterials, vol. 28, pp. 1280-1288, 2007.
Longmire, et al., "Clearance properties of nano sized particles and molecules as imaging agents: considerations and caveats," Nanomedicine, vol. 3, pp. 703-717, 2008.
McNamara, et al., "Cell type specific delivery of siRNAs with aptamer siRNA chimeras," Nat. Biotechnol., vol. 24, pp. 1005-1015, 2006.
Medarova, et al., "In vivo imaging of siRNA delivery and silencing in tumors," Nat. Med., vol. 13, pp. 372-377, 2007.
Meng, et al., "Engineered design of mesoporous silica nanoparticles to deliver doxorubicin and P glycoprotein siRNA to overcome drug resistance in a cancer cell line," ACS Nano, vol. 4, pp. 4539-4550, 2010.
Midoux, et al., "Chemical vectors for gene delivery: a current review on polymers, peptides and lipids containing histidine or imidazole as nucleic acids carriers," Br. J. Pharmacol., vol. 157, pp. 166-178, 2009.
Moschos, et al., Lung delivery studies using siRNA conjugated to TAT (4860) and penetratin reveal peptide induced reduction in gene expression and induction of innate immunity, Bioconjug. Chem., vol. 18, pp. 1450-1459, 2007.
Nallagatla, et al., "Nucleoside modifications modulate activation of the protein kinase PKR in an RNA structure specific manner," RNA, vol. 14, pp. 1201-1213, 2008.
Nanduri, et al., "Structure of the double stranded RNA binding domain of the protein kinase PKR reveals the molecular basis of its dsRNA mediated activation," Embo Journal, vol. 17, pp. 5458-5465, 1998.
Nishina, et al., "Efficient in vivo delivery of siRNA to the liver by conjugation of alpha tocopherol.," Mol. Ther., vol. 16, pp. 734-740, 2008.
Pichon, et al., "Histidine rich peptides and polymers for nucleic acids delivery," Adv. Drug Del. Rev., vol. 53, pp. 75-94, 2001.
Pirollo et al., "Targeted Delivery of small interfereing RNA: Approaching effective Cancer therapies," Cancer Res., vol. 68, No. 1247, 2008.
Probst, et al., "Quantum dots as a platform for nanoparticle drug delivery vehicle design" Adv. Drug Del. Rev., vol. 65, pp. 703-718, 2013.
Qi, et al., "Emerging application of quantum dots for drug delivery and therapy," Exp. Opin. Drug Del, vol. 5, pp. 263-267, 2008.
Qi, et al., "Quantum dot amphipol nanocomplex for intracellular delivery and real time imaging of siRNA," ACS Nano 2, pp. 1403-1410, 2008.
Reich, et al., "Small interfering RNA (siRNA) targeting VEGF effectively inhibits ocular neovascularization in a mouse model," Mol. Vision, vol. 9, pp. 210-216, 2003.
RNAi Drug Delivery: Technologies and Global Markets. BCC Research. [Online] Jan. 2011. [Cited: Dec. 7, 2013.], downloaded from the Internet at http://www.bccresearch.com/market-research/biotechnology/mai-drug-delivery-tech-markets-bio076a.html, 2011.
Scherer, et al., "Approaches for the sequence specific knockdown of mRNA," Nal Biotechnol. vol. 21, pp. 1457-1465, 2003.
Soutschek, et al., "Therapeutic silencing of an endogenous gene by systemic administration of modified siRNAs." Nature, vol. 432, pp. 173-178, 2004.
Varkouhi, et al., "Endosomal escape pathways for delivery of biologicals," Journal of Controlled Release, vol. 151, No. 3, 2010.
Walter, et al., "Systematic investigation of optimal aptamer immobilization for protein microarray applications," Anal. Chem., vol. 80, pp. 7372-7378, 2008.
Whitehead, et al., "Knocking down barriers: advances in siRNA delivery," Nat. Rev. Drug Discov., vol. 8, pp. 129-138, 2009.
Wolfrum,C. et al., "Mechanisms and optimization of in vivo delivery of lipophilic siRNAs," Nat. Biotechnol., vol. 25, pp. 1149-1157, 2007.
Xia, et al., "Polyethyleneimine coating enhances the cellular uptake of mesoporous silica nanoparticles and allows safe delivery of siRNA and DNA constructs," ACS Nano, vol. 3, pp. 3273-3286, 2009.

\* cited by examiner

SEQUENCE LISTING

```
<160> NUMBER OF SEQ ID NOS: 99

<210> SEQ ID NO 1
<211> LENGTH: 70
<212> TYPE: PRT
<213> ORGANISM: Homo sapiens

<400> SEQUENCE: 1

Phe Phe Met Glu Glu Leu Asn Thr Tyr Arg Gln Lys Gln Gly Val Val
1               5                   10                  15

Leu Lys Tyr Gln Glu Leu Pro Asn Ser Gly Pro Pro His Asp Arg Arg
            20                  25                  30

Phe Thr Phe Gln Val Ile Ile Asp Gly Arg Glu Phe Pro Glu Gly Glu
        35                  40                  45

Gly Arg Ser Lys Lys Glu Ala Lys Asn Ala Ala Ala Lys Leu Ala Val
    50                  55                  60

Glu Ile Leu Asn Lys Glu
65                  70

<210> SEQ ID NO 2
<211> LENGTH: 69
<212> TYPE: PRT
<213> ORGANISM: Homo sapiens

<400> SEQUENCE: 2

Asn Tyr Ile Gly Leu Ile Asn Arg Ile Ala Gln Lys Lys Arg Leu Thr
1               5                   10                  15

Val Asn Tyr Glu Gln Cys Ala Ser Gly Val His Gly Pro Glu Gly Phe
            20                  25                  30

His Tyr Lys Cys Lys Met Gly Gln Lys Glu Tyr Ser Ile Gly Ile Gly
        35                  40                  45

Ser Thr Lys Gln Glu Ala Lys Gln Ile Ala Ala Lys Leu Ala Tyr Leu
    50                  55                  60

Gln Ile Leu Ser Glu
65

<210> SEQ ID NO 3
<211> LENGTH: 70
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: MISC_FEATURE
<222> LOCATION: (2)..(2)
<223> OTHER INFORMATION: Xaa is F or Y
<220> FEATURE:
<221> NAME/KEY: MISC_FEATURE
<222> LOCATION: (3)..(5)
```

```
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is L or I
<220> FEATURE:
<221> NAME/KEY: MISC_FEATURE
<222> LOCATION: (8)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is Y or I
<220> FEATURE:
<221> NAME/KEY: MISC_FEATURE
<222> LOCATION: (10)..(10)
<223> OTHER INFORMATION: Xaa is any amino acid
<220> FEATURE:
<221> NAME/KEY: MISC_FEATURE
<222> LOCATION: (13)..(14)
<223> OTHER INFORMATION: Xaa is any amino acid
<220> FEATURE:
<221> NAME/KEY: MISC_FEATURE
<222> LOCATION: (15)..(15)
<223> OTHER INFORMATION: Xaa is V or L
<220> FEATURE:
<221> NAME/KEY: MISC_FEATURE
<222> LOCATION: (16)..(16)
<223> OTHER INFORMATION: Xaa is any amino acid
<220> FEATURE:
<221> NAME/KEY: MISC_FEATURE
<222> LOCATION: (17)..(17)
<223> OTHER INFORMATION: Xaa is V or L
<220> FEATURE:
<221> NAME/KEY: MISC_FEATURE
<222> LOCATION: (18)..(18)
<223> OTHER INFORMATION: Xaa is any amino acid
<220> FEATURE:
<221> NAME/KEY: MISC_FEATURE
<222> LOCATION: (20)..(25)
<223> OTHER INFORMATION: Xaa is any amino acid
<220> FEATURE:
<221> NAME/KEY: MISC_FEATURE
<222> LOCATION: (27)..(32)
<223> OTHER INFORMATION: Xaa is any amino acid
<220> FEATURE:
<221> NAME/KEY: MISC_FEATURE
<222> LOCATION: (34)..(34)
<223> OTHER INFORMATION: Xaa is any amino acid
<220> FEATURE:
<221> NAME/KEY: MISC_FEATURE
<222> LOCATION: (35)..(35)
<223> OTHER INFORMATION: Xaa is F or Y
<220> FEATURE:
<221> NAME/KEY: MISC_FEATURE
<222> LOCATION: (36)..(38)
<223> OTHER INFORMATION: Xaa is any amino acid
<220> FEATURE:
<221> NAME/KEY: MISC_FEATURE
<222> LOCATION: (39)..(39)
<223> OTHER INFORMATION: Xaa is I or M
<220> FEATURE:
<221> NAME/KEY: MISC_FEATURE
<222> LOCATION: (40)..(41)
<223> OTHER INFORMATION: Xaa is any amino acid
<220> FEATURE:
<221> NAME/KEY: MISC_FEATURE
<222> LOCATION: (42)..(42)
<223> OTHER INFORMATION: Xaa is R or K
<220> FEATURE:
<221> NAME/KEY: MISC_FEATURE
<222> LOCATION: (44)..(44)
<223> OTHER INFORMATION: Xaa is F or Y
<220> FEATURE:
<221> NAME/KEY: MISC_FEATURE
<222> LOCATION: (45)..(46)
<223> OTHER INFORMATION: Xaa is any amino acid
<220> FEATURE:
<221> NAME/KEY: MISC_FEATURE
```

```
<222> LOCATION: (48)..(48)
<223> OTHER INFORMATION: Xaa is any amino acid
<220> FEATURE:
<221> NAME/KEY: MISC_FEATURE
<222> LOCATION: (50)..(50)
<223> OTHER INFORMATION: Xaa is any amino acid
<220> FEATURE:
<221> NAME/KEY: MISC_FEATURE
<222> LOCATION: (51)..(51)
<223> OTHER INFORMATION: Xaa is S or T
<220> FEATURE:
<221> NAME/KEY: MISC_FEATURE
<222> LOCATION: (53)..(53)
<223> OTHER INFORMATION: Xaa is any amino acid
<220> FEATURE:
<221> NAME/KEY: MISC_FEATURE
<222> LOCATION: (57)..(57)
<223> OTHER INFORMATION: Xaa is N or Q
<220> FEATURE:
<221> NAME/KEY: MISC_FEATURE
<222> LOCATION: (58)..(58)
<223> OTHER INFORMATION: Xaa is any amino acid
<220> FEATURE:
<221> NAME/KEY: MISC_FEATURE
<222> LOCATION: (64)..(64)
<223> OTHER INFORMATION: Xaa is V or Y
<220> FEATURE:
<221> NAME/KEY: MISC_FEATURE
<222> LOCATION: (65)..(66)
<223> OTHER INFORMATION: Xaa is any amino acid
<220> FEATURE:
<221> NAME/KEY: MISC_FEATURE
<222> LOCATION: (67)..(67)
<223> OTHER INFORMATION: Xaa is L or I
<220> FEATURE:
<221> NAME/KEY: MISC_FEATURE
<222> LOCATION: (68)..(69)
<223> OTHER INFORMATION: Xaa is any amino acid

<400> SEQUENCE: 3

Xaa Xaa Xaa Xaa Xaa Xaa Asn Xaa Xaa Xaa Gln Lys Xaa Xaa Xaa Xaa
1               5                   10                  15

Xaa Xaa Tyr Xaa Xaa Xaa Xaa Xaa Xaa Gly Xaa Xaa Xaa Xaa Xaa Xaa
            20                  25                  30

Phe Xaa Xaa Xaa Xaa Xaa Xaa Xaa Xaa Xaa Glu Xaa Xaa Xaa Gly Xaa
        35                  40                  45

Gly Xaa Xaa Lys Xaa Glu Ala Lys Xaa Xaa Ala Ala Lys Leu Ala Xaa
    50                  55                  60

Xaa Xaa Xaa Xaa Xaa Glu
65                  70

<210> SEQ ID NO 4
<211> LENGTH: 68
<212> TYPE: PRT
<213> ORGANISM: Drosophila melanogaster

<400> SEQUENCE: 4

Thr Pro Met Cys Leu Val Asn Glu Leu Ala Arg Tyr Asn Lys Ile Thr
1               5                   10                  15

His Gln Tyr Arg Leu Thr Glu Glu Arg Gly Pro Ala His Cys Lys Thr
            20                  25                  30

Phe Thr Val Thr Leu Met Leu Gly Asp Glu Glu Tyr Ser Ala Asp Gly
        35                  40                  45

Phe Lys Ile Lys Lys Ala Gln His Leu Ala Ala Ser Lys Ala Ile Glu
    50                  55                  60

Glu Thr Met Tyr
65
```

<210> SEQ ID NO 5
<211> LENGTH: 68
<212> TYPE: PRT
<213> ORGANISM: Drosophila melanogaster

<400> SEQUENCE: 5

Ser Pro Ile Ser Gln Val His Glu Ile Gly Ile Lys Arg Asn Met Thr
1               5                   10                  15

Val His Phe Lys Val Leu Arg Glu Gly Pro Ala His Met Lys Asn
            20                  25                  30

Phe Ile Thr Ala Cys Ile Val Gly Ser Ile Val Thr Glu Gly Glu Gly
            35                  40                  45

Asn Gly Lys Lys Val Ser Lys Arg Ala Ala Glu Lys Met Leu Val
        50                  55                  60

Glu Leu Gln Lys
65

<210> SEQ ID NO 6
<211> LENGTH: 71
<212> TYPE: PRT
<213> ORGANISM: Drosophila melanogaster

<400> SEQUENCE: 6

Asn Pro Ile Thr Lys Leu Ile Gln Leu Gln Gln Thr Arg Lys Glu Lys
1               5                   10                  15

Glu Pro Ile Phe Glu Leu Ile Ala Lys Asn Gly Asn Glu Thr Ala Arg
            20                  25                  30

Arg Arg Glu Phe Val Met Glu Val Ser Ala Ser Gly Ser Thr Ala Arg
            35                  40                  45

Gly Thr Gly Asn Ser Lys Lys Leu Ala Lys Arg Asn Ala Ala Gln Ala
        50                  55                  60

Leu Phe Glu Leu Leu Glu Ala
65                  70

<210> SEQ ID NO 7
<211> LENGTH: 69
<212> TYPE: PRT
<213> ORGANISM: Homo sapiens

<400> SEQUENCE: 7

Phe Phe Met Glu Glu Leu Asn Thr Tyr Arg Gln Lys Gln Gly Val Val
1               5                   10                  15

Leu Lys Tyr Gln Glu Leu Pro Asn Ser Gly Pro Pro His Asp Arg Arg
            20                  25                  30

Phe Thr Phe Gln Val Ile Ile Asp Gly Arg Glu Phe Pro Glu Gly Glu
            35                  40                  45

Gly Arg Ser Lys Lys Glu Ala Lys Asn Ala Ala Ala Lys Leu Ala Val
        50                  55                  60

Glu Ile Leu Asn Lys
65

<210> SEQ ID NO 8
<211> LENGTH: 68
<212> TYPE: PRT
<213> ORGANISM: Homo sapiens

<400> SEQUENCE: 8

Asn Tyr Ile Gly Leu Ile Asn Arg Ile Ala Gln Lys Lys Arg Leu Thr
1               5                   10                  15

```
Val Asn Tyr Glu Gln Cys Ala Ser Gly Val His Gly Pro Glu Gly Phe
            20                  25                  30

His Tyr Lys Cys Lys Met Gly Gln Lys Glu Tyr Ser Ile Gly Thr Gly
                35                  40                  45

Ser Thr Lys Gln Glu Ala Lys Gln Leu Ala Ala Lys Leu Ala Tyr Leu
    50                  55                  60

Gln Ile Leu Ser
65

<210> SEQ ID NO 9
<211> LENGTH: 68
<212> TYPE: PRT
<213> ORGANISM: Homo sapiens

<400> SEQUENCE: 9

Thr Pro Ile Gln Val Leu His Glu Tyr Gly Met Lys Thr Lys Asn Ile
1               5                   10                  15

Pro Val Tyr Glu Cys Glu Arg Ser Asp Val Gln Ile His Val Pro Thr
            20                  25                  30

Phe Thr Phe Arg Val Thr Val Gly Asp Ile Thr Cys Thr Gly Glu Gly
                35                  40                  45

Thr Ser Lys Lys Leu Ala Lys His Arg Ala Ala Glu Ala Ala Ile Asn
    50                  55                  60

Ile Leu Lys Ala
65

<210> SEQ ID NO 10
<211> LENGTH: 69
<212> TYPE: PRT
<213> ORGANISM: Homo sapiens

<400> SEQUENCE: 10

Asn Pro Ile Gly Ser Leu Gln Glu Leu Ala Ile His His Gly Trp Arg
1               5                   10                  15

Leu Pro Glu Tyr Thr Leu Ser Gln Glu Gly Gly Pro Ala His Lys Arg
            20                  25                  30

Glu Tyr Thr Thr Ile Cys Arg Leu Glu Ser Phe Met Glu Thr Gly Lys
                35                  40                  45

Gly Ala Ser Lys Lys Gln Ala Lys Arg Asn Ala Ala Glu Lys Phe Leu
    50                  55                  60

Ala Lys Phe Ser Asn
65

<210> SEQ ID NO 11
<211> LENGTH: 68
<212> TYPE: PRT
<213> ORGANISM: Xenopus laevis

<400> SEQUENCE: 11

Thr Pro Ile Gln Leu Leu His Glu Phe Gly Thr Lys Thr Gly Asn His
1               5                   10                  15

Pro Val Tyr Thr Leu Glu Lys Ala Glu Gly Gln Ala His Asn Pro Ser
            20                  25                  30

Phe Thr Phe Arg Leu Val Ile Gly Asp Ile Thr Ser Leu Gly Glu Gly
                35                  40                  45

Pro Ser Lys Lys Thr Pro Lys Gln Lys Ala Ala Glu Phe Ala Leu Asn
    50                  55                  60
```

```
Ile Leu Arg Gly
65

<210> SEQ ID NO 12
<211> LENGTH: 69
<212> TYPE: PRT
<213> ORGANISM: Xenopus laevis

<400> SEQUENCE: 12

Asn Pro Val Gly Ser Leu Gln Glu Leu Ala Val Gln Lys Gly Trp Arg
1               5                   10                  15

Leu Pro Glu Tyr Thr Val Ala Gln Glu Ser Gly Pro Pro His Lys Arg
                20                  25                  30

Glu Phe Thr Ile Thr Cys Arg Val Glu Thr Phe Val Glu Thr Gly Ser
            35                  40                  45

Gly Thr Ser Lys Gln Val Ala Lys Arg Val Ala Glu Lys Leu Leu
        50                  55                  60

Thr Lys Phe Lys Thr
65

<210> SEQ ID NO 13
<211> LENGTH: 68
<212> TYPE: PRT
<213> ORGANISM: Homo sapiens

<400> SEQUENCE: 13

Thr Pro Ile Ser Leu Leu Gln Glu Tyr Gly Thr Arg Ile Gly Lys Thr
1               5                   10                  15

Pro Val Tyr Asp Leu Leu Lys Ala Glu Gly Gln Ala His Gln Pro Asn
                20                  25                  30

Phe Thr Phe Arg Val Thr Val Gly Asp Thr Ser Cys Thr Gly Gln Gly
            35                  40                  45

Pro Ser Lys Lys Ala Ala Lys His Lys Ala Ala Glu Val Ala Leu Lys
        50                  55                  60

His Leu Lys Gly
65

<210> SEQ ID NO 14
<211> LENGTH: 69
<212> TYPE: PRT
<213> ORGANISM: Homo sapiens

<400> SEQUENCE: 14

Asn Pro Val Gly Ala Leu Gln Glu Leu Val Val Gln Lys Gly Trp Arg
1               5                   10                  15

Leu Pro Glu Tyr Thr Val Thr Gln Glu Ser Gly Pro Ala His Arg Lys
                20                  25                  30

Glu Phe Thr Met Thr Cys Arg Val Glu Arg Phe Ile Glu Ile Gly Ser
            35                  40                  45

Gly Thr Ser Lys Lys Leu Ala Lys Arg Asn Ala Ala Lys Met Leu
        50                  55                  60

Leu Arg Val His Thr
65

<210> SEQ ID NO 15
<211> LENGTH: 68
<212> TYPE: PRT
<213> ORGANISM: Homo sapiens

<400> SEQUENCE: 15
```

```
Ser Glu Val Cys Ile Leu His Glu Tyr Met Gln Arg Val Leu Lys Val
1               5                   10                  15

Arg Pro Val Tyr Asn Phe Phe Glu Cys Glu Asn Pro Ser Glu Pro Phe
                20                  25                  30

Gly Ala Ser Val Thr Ile Asp Gly Val Thr Tyr Gly Ser Gly Thr Ala
            35                  40                  45

Ser Ser Lys Lys Leu Ala Lys Asn Lys Ala Ala Arg Ala Thr Leu Glu
        50                  55                  60

Ile Leu Ile Pro
65

<210> SEQ ID NO 16
<211> LENGTH: 68
<212> TYPE: PRT
<213> ORGANISM: Homo sapiens

<400> SEQUENCE: 16

Ser Pro Tyr Gln Ile Leu His Glu Cys Leu Lys Arg Asn His Gly Met
1               5                   10                  15

Gly Asp Thr Ser Ile Lys Phe Glu Val Val Pro Gly Lys Asn Gln Lys
                20                  25                  30

Ser Glu Tyr Val Met Ala Cys Gly Lys His Thr Val Arg Gly Trp Cys
            35                  40                  45

Lys Asn Lys Arg Val Gly Lys Gln Leu Ala Ser Gln Lys Ile Leu Gln
        50                  55                  60

Leu Leu His Pro
65

<210> SEQ ID NO 17
<211> LENGTH: 69
<212> TYPE: PRT
<213> ORGANISM: Homo sapiens

<400> SEQUENCE: 17

Asn Pro Ile Ser Gly Leu Leu Glu Tyr Ala Gln Phe Ala Ser Gln Thr
1               5                   10                  15

Cys Glu Phe Asn Met Ile Glu Gln Ser Gly Pro Pro His Glu Pro Arg
                20                  25                  30

Phe Lys Phe Gln Val Val Ile Asn Gly Arg Glu Phe Pro Pro Ala Glu
            35                  40                  45

Ala Gly Ser Lys Lys Val Ala Lys Gln Asp Ala Ala Met Lys Ala Met
        50                  55                  60

Thr Ile Leu Leu Glu
65

<210> SEQ ID NO 18
<211> LENGTH: 69
<212> TYPE: PRT
<213> ORGANISM: Homo sapiens

<400> SEQUENCE: 18

Ser Pro Val Thr Thr Leu Leu Glu Cys Met His Lys Leu Gly Asn Ser
1               5                   10                  15

Cys Glu Phe Arg Leu Leu Ser Lys Glu Gly Pro Ala His Glu Pro Lys
                20                  25                  30

Phe Gln Tyr Cys Val Ala Val Gly Ala Gln Thr Phe Pro Ser Val Ser
            35                  40                  45
```

```
Ala Pro Ser Lys Lys Val Ala Lys Gln Met Ala Ala Glu Glu Ala Met
 50                  55                  60

Lys Ala Leu His Gly
 65
```

<210> SEQ ID NO 19
<211> LENGTH: 64
<212> TYPE: PRT
<213> ORGANISM: Homo sapiens

<400> SEQUENCE: 19

```
Asn Ala Leu Met Gln Leu Asn Glu Ile Lys Pro Gly Leu Gln Tyr Thr
 1               5                  10                  15

Leu Leu Ser Gln Thr Gly Pro Val His Ala Pro Leu Phe Val Met Ser
             20                  25                  30

Val Glu Val Asn Gly Gln Val Phe Glu Gly Ser Gly Pro Thr Lys Lys
         35                  40                  45

Lys Ala Lys Leu His Ala Ala Glu Lys Ala Leu Arg Ser Phe Val Gln
     50                  55                  60
```

<210> SEQ ID NO 20
<211> LENGTH: 64
<212> TYPE: PRT
<213> ORGANISM: Homo sapiens

<400> SEQUENCE: 20

```
Asn Pro Val Met Ile Leu Asn Glu Leu Arg Pro Gly Leu Lys Tyr Asp
 1               5                  10                  15

Phe Leu Ser Glu Ser Gly Glu Ser His Ala Lys Ser Phe Val Met Ser
             20                  25                  30

Val Val Val Asp Gly Gln Phe Phe Glu Gly Ser Gly Arg Asn Lys Lys
         35                  40                  45

Leu Ala Lys Ala Arg Ala Ala Gln Ser Ala Leu Ala Ala Ile Phe Asn
     50                  55                  60
```

<210> SEQ ID NO 21
<211> LENGTH: 64
<212> TYPE: PRT
<213> ORGANISM: Drosophila melanogaster

<400> SEQUENCE: 21

```
Asn Thr Val Ala Met Leu Asn Glu Leu Arg His Gly Leu Ile Tyr Lys
 1               5                  10                  15

Leu Glu Ser Gln Thr Gly Pro Val His Ala Pro Leu Phe Thr Ile Ser
             20                  25                  30

Val Glu Val Asp Gly Gln Lys Tyr Leu Gly Gln Gly Arg Ser Lys Lys
         35                  40                  45

Val Ala Arg Ile Glu Ala Ala Thr Ala Leu Arg Ser Phe Ile Gly
     50                  55                  60
```

<210> SEQ ID NO 22
<211> LENGTH: 64
<212> TYPE: PRT
<213> ORGANISM: Drosophila melanogaster

<400> SEQUENCE: 22

```
Gly Pro Val Met Leu Leu Tyr Glu Leu Phe Asn Asp Val Asn Phe Glu
 1               5                  10                  15

Cys Ile Asn Ile Asp Gly Ala Gln Asn Asn Cys Arg Phe Lys Met Thr
             20                  25                  30
```

Val Thr Ile Asn Glu Lys Lys Phe Asp Gly Thr Gly Pro Ser Lys Lys
         35                  40                  45

Thr Ala Lys Asn Ala Ala Ala Lys Ala Ala Leu Ala Ser Leu Cys Asn
     50                  55                  60

<210> SEQ ID NO 23
<211> LENGTH: 63
<212> TYPE: PRT
<213> ORGANISM: Homo sapiens

<400> SEQUENCE: 23

Ser Pro Val Arg Glu Leu Leu Glu Met Glu Pro Glu Thr Ala Lys Phe
1               5                   10                  15

Ser Pro Ala Glu Arg Thr Tyr Asp Gly Lys Val Arg Val Thr Val Glu
            20                  25                  30

Val Val Gly Lys Gly Lys Phe Lys Gly Val Gly Arg Ser Tyr Arg Ile
        35                  40                  45

Ala Lys Ser Ala Ala Ala Arg Arg Ala Leu Arg Ser Leu Lys Ala
     50                  55                  60

<210> SEQ ID NO 24
<211> LENGTH: 69
<212> TYPE: PRT
<213> ORGANISM: Saccharomyces cerevisiae

<400> SEQUENCE: 24

Asn Ala Lys Arg Gln Leu Tyr Ser Leu Ile Gly Tyr Ala Ser Leu Arg
1               5                   10                  15

Leu His Tyr Val Thr Val Lys Lys Pro Thr Ala Val Asp Pro Asn Ser
            20                  25                  30

Ile Val Glu Cys Arg Val Gly Asp Gly Thr Val Leu Gly Thr Gly Val
        35                  40                  45

Gly Arg Asn Ile Lys Ile Ala Gly Ile Arg Ala Ala Glu Asn Ala Leu
     50                  55                  60

Arg Asp Lys Lys Met
65

<210> SEQ ID NO 25
<211> LENGTH: 72
<212> TYPE: PRT
<213> ORGANISM: Escherichia coli

<400> SEQUENCE: 25

Asp Pro Lys Thr Arg Leu Gln Glu Tyr Leu Gln Gly Arg His Leu Pro
1               5                   10                  15

Leu Pro Thr Tyr Leu Val Val Gln Val Arg Gly Glu Ala His Asp Gln
            20                  25                  30

Glu Phe Thr Thr Ile His Cys Gln Val Ser Gly Leu Ser Glu Pro Val
        35                  40                  45

Val Gly Thr Gly Ser Ser Arg Arg Lys Ala Glu Gln Ala Ala Ala Glu
     50                  55                  60

Gln Ala Leu Lys Lys Leu Glu Leu
65                  70

<210> SEQ ID NO 26
<211> LENGTH: 69
<212> TYPE: PRT
<213> ORGANISM: Aquifex pyrophilus

```
<400> SEQUENCE: 26

Asp Tyr Lys Thr Ile Leu Gln Glu Ile Thr Gln Lys Arg Trp Lys Glu
1               5                   10                  15

Arg Pro Glu Tyr Arg Leu Ile Ser Val Gly Pro His His Lys Lys
            20                  25                  30

Lys Phe Ile Val Glu Ala Lys Ile Lys Glu Tyr Arg Thr Leu Gly Glu
                35                  40                  45

Gly Lys Ser Lys Lys Glu Ala Glu Gln Arg Ala Ala Glu Glu Leu Ile
        50                  55                  60

Lys Leu Leu Glu Glu
65

<210> SEQ ID NO 27
<211> LENGTH: 70
<212> TYPE: PRT
<213> ORGANISM: Arabidopsis thaliana

<400> SEQUENCE: 27

Val Phe Lys Ser Arg Leu Gln Glu Tyr Ala Gln Lys Tyr Lys Leu Pro
1               5                   10                  15

Thr Pro Val Tyr Glu Ile Val Lys Glu Gly Pro Ser His Lys Ser Leu
            20                  25                  30

Phe Gln Ser Thr Val Ile Leu Asp Gly Val Arg Tyr Asn Ser Leu Pro
                35                  40                  45

Gly Phe Phe Asn Arg Lys Ala Ala Glu Gln Ser Ala Ala Glu Val Ala
        50                  55                  60

Leu Arg Glu Leu Ala Lys
65                  70

<210> SEQ ID NO 28
<211> LENGTH: 70
<212> TYPE: PRT
<213> ORGANISM: Arabidopsis thaliana

<400> SEQUENCE: 28

Leu Cys Lys Asn Leu Leu Gln Glu Tyr Ala Gln Lys Met Asn Tyr Ala
1               5                   10                  15

Ile Pro Leu Tyr Gln Cys Gln Lys Val Glu Thr Leu Gly Arg Val Thr
            20                  25                  30

Gln Phe Thr Cys Thr Val Glu Ile Gly Gly Ile Lys Tyr Thr Gly Ala
                35                  40                  45

Ala Thr Arg Thr Lys Lys Asp Ala Glu Ile Ser Ala Gly Arg Thr Ala
        50                  55                  60

Leu Leu Ala Ile Gln Ser
65                  70

<210> SEQ ID NO 29
<211> LENGTH: 72
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: MISC_FEATURE
<222> LOCATION: (3)..(5)
<223> OTHER INFORMATION: Xaa is any amino acid
<220> FEATURE:
```

<221> NAME/KEY: MISC_FEATURE
<222> LOCATION: (7)..(7)
<223> OTHER INFORMATION: Xaa is any amino acid
<220> FEATURE:
<221> NAME/KEY: MISC_FEATURE
<222> LOCATION: (10)..(18)
<223> OTHER INFORMATION: Xaa is any amino acid
<220> FEATURE:
<221> NAME/KEY: MISC_FEATURE
<222> LOCATION: (20)..(20)
<223> OTHER INFORMATION: Xaa is any amino acid
<220> FEATURE:
<221> NAME/KEY: MISC_FEATURE
<222> LOCATION: (22)..(27)
<223> OTHER INFORMATION: Xaa is any amino acid
<220> FEATURE:
<221> NAME/KEY: MISC_FEATURE
<222> LOCATION: (30)..(30)
<223> OTHER INFORMATION: Xaa is any amino acid
<220> FEATURE:
<221> NAME/KEY: MISC_FEATURE
<222> LOCATION: (32)..(34)
<223> OTHER INFORMATION: Xaa is any amino acid
<220> FEATURE:
<221> NAME/KEY: MISC_FEATURE
<222> LOCATION: (36)..(38)
<223> OTHER INFORMATION: Xaa is any amino acid
<220> FEATURE:
<221> NAME/KEY: MISC_FEATURE
<222> LOCATION: (40)..(40)
<223> OTHER INFORMATION: Xaa is any amino acid
<220> FEATURE:
<221> NAME/KEY: MISC_FEATURE
<222> LOCATION: (42)..(42)
<223> OTHER INFORMATION: Xaa is any amino acid
<220> FEATURE:
<221> NAME/KEY: MISC_FEATURE
<222> LOCATION: (44)..(49)
<223> OTHER INFORMATION: Xaa is any amino acid
<220> FEATURE:
<221> NAME/KEY: MISC_FEATURE
<222> LOCATION: (51)..(51)
<223> OTHER INFORMATION: Xaa is any amino acid
<220> FEATURE:
<221> NAME/KEY: MISC_FEATURE
<222> LOCATION: (53)..(53)
<223> OTHER INFORMATION: Xaa is any amino acid
<220> FEATURE:
<221> NAME/KEY: MISC_FEATURE
<222> LOCATION: (57)..(57)
<223> OTHER INFORMATION: Xaa is any amino acid
<220> FEATURE:
<221> NAME/KEY: MISC_FEATURE
<222> LOCATION: (60)..(61)
<223> OTHER INFORMATION: Xaa is any amino acid
<220> FEATURE:
<221> NAME/KEY: MISC_FEATURE
<222> LOCATION: (65)..(65)
<223> OTHER INFORMATION: Xaa is any amino acid
<220> FEATURE:
<221> NAME/KEY: MISC_FEATURE
<222> LOCATION: (68)..(69)
<223> OTHER INFORMATION: Xaa is any amino acid
<220> FEATURE:
<221> NAME/KEY: MISC_FEATURE
<222> LOCATION: (71)..(72)
<223> OTHER INFORMATION: Xaa is any amino acid

<400> SEQUENCE: 29

Xaa Pro Xaa Xaa Xaa Leu Xaa Glu Leu Xaa Xaa Xaa Xaa Xaa Xaa
 1               5                  10                  15

Xaa Xaa Pro Xaa Tyr Xaa Xaa Xaa Xaa Xaa Xaa Gly Pro Xaa His Xaa
                20                  25                  30

Xaa Xaa Phe Xaa Xaa Xaa Val Xaa Val Xaa Gly Xaa Xaa Xaa Xaa Xaa
            35                  40                  45

```
Xaa Gly Xaa Gly Xaa Ser Lys Lys Xaa Ala Lys Xaa Xaa Ala Ala Glu
        50                  55                  60

Xaa Ala Leu Xaa Xaa Leu Xaa Xaa
 65                  70
```

<210> SEQ ID NO 30
<211> LENGTH: 64
<212> TYPE: PRT
<213> ORGANISM: Homo sapiens

<400> SEQUENCE: 30

```
Pro Lys Met Cys Leu Leu Glu Trp Cys Arg Arg Glu Lys Leu Ala Gln
 1               5                  10                  15

Pro Val Tyr Glu Thr Val Gln Arg Pro Leu Asp Arg Leu Phe Ser Ser
             20                  25                  30

Ile Val Thr Val Ala Glu Gln Lys Tyr Gln Ser Thr Leu Trp Asp Lys
         35                  40                  45

Ser Lys Lys Leu Ala Gly Gln Ala Ala Ala Ile Val Cys Leu Arg Ser
     50                  55                  60
```

<210> SEQ ID NO 31
<211> LENGTH: 64
<212> TYPE: PRT
<213> ORGANISM: Mus musculus

<400> SEQUENCE: 31

```
Pro Lys Met Cys Leu Leu Glu Trp Cys Arg Arg Glu Lys Leu Pro Gln
 1               5                  10                  15

Pro Val Tyr Glu Thr Val Gln Arg Thr Ile Asp Arg Met Phe Cys Ser
             20                  25                  30

Val Val Thr Val Ala Glu Gln Lys Tyr Gln Ser Thr Leu Trp Asp Lys
         35                  40                  45

Ser Lys Lys Leu Ala Gly Gln Thr Ala Ala Ile Val Cys Leu Arg Ser
     50                  55                  60
```

<210> SEQ ID NO 32
<211> LENGTH: 63
<212> TYPE: PRT
<213> ORGANISM: Drosophila melanogaster

<400> SEQUENCE: 32

```
Pro Phe Leu Arg Ser Thr Tyr Pro Ser Asp Asn His Leu Pro Lys Thr
 1               5                  10                  15

Gln Leu Tyr Val His Ala Val Lys Thr Gly Lys Ser Pro Pro Ala Tyr
             20                  25                  30

Glu Thr Gln Gln Cys Asp Lys Leu Phe Arg Ser Ile Cys Thr Tyr Asp
         35                  40                  45

Gly Gln Arg Phe Ser Ser Ser Phe Trp Glu Lys Asn Lys Lys Gln
     50                  55                  60
```

<210> SEQ ID NO 33
<211> LENGTH: 62
<212> TYPE: PRT
<213> ORGANISM: Anopheles gambiae

<400> SEQUENCE: 33

```
Arg Phe Asp Gly Gln Arg Tyr Thr Ser Ser Phe Trp Glu Lys Asn Lys
 1               5                  10                  15

Arg Tyr Ala Glu Gln Ala Ala Ala Leu Val Cys Leu Leu Lys Arg Gly
             20                  25                  30
```

```
Val Glu Ser Arg Asp Glu Leu Ile Arg Asn Gly Ala Met Leu Pro Ala
        35                  40                  45

Lys Asn Gly Pro Ala Ala Ala Val Val Glu Leu Thr Asp Ser
 50                  55                  60
```

<210> SEQ ID NO 34
<211> LENGTH: 64
<212> TYPE: PRT
<213> ORGANISM: Caenorhabditis elegans

<400> SEQUENCE: 34

```
Pro Lys Met Val Leu His Asp Tyr Cys Val Glu Thr Lys Ile Pro Lys
 1               5                  10                  15

Ala Thr Tyr Glu Val Val Lys Arg Asp Asp Lys Arg Phe Val Ala Thr
            20                  25                  30

Ala Cys Ile Gly Asp Lys Lys Tyr Arg Ser Gly Ile Gly Gln Pro Asn
        35                  40                  45

Leu Arg Met Ala Glu Gln Val Ala Leu Ala Ala Leu His Gly Met
 50                  55                  60
```

<210> SEQ ID NO 35
<211> LENGTH: 69
<212> TYPE: PRT
<213> ORGANISM: Homo sapiens

<400> SEQUENCE: 35

```
Val Glu Ala Leu Gln Glu Phe Trp Gln Met Lys Gln Ser Arg Gly Ala
 1               5                  10                  15

Asp Leu Lys Asn Gly Ala Leu Val Val Tyr Glu Met Val Pro Ser Asn
            20                  25                  30

Ser Pro Pro Tyr Val Cys Tyr Val Thr Leu Pro Gly Gly Ser Cys Phe
        35                  40                  45

Gly Ser Phe Gln Phe Cys Pro Thr Lys Ala Glu Ala Arg Arg Ser Ala
 50                  55                  60

Ala Lys Ile Ala Leu
 65
```

<210> SEQ ID NO 36
<211> LENGTH: 69
<212> TYPE: PRT
<213> ORGANISM: Mus musculus

<400> SEQUENCE: 36

```
Val Glu Ala Leu Gln Glu Phe Trp Gln Met Lys Gln Ser Arg Gly Ala
 1               5                  10                  15

Asp Leu Lys Asn Gly Ala Leu Val Val Tyr Glu Met Val Pro Ser Asn
            20                  25                  30

Ser Pro Pro Tyr Val Cys Tyr Val Thr Leu Pro Gly Gly Ser Cys Phe
        35                  40                  45

Gly Ser Phe Gln Phe Cys Pro Thr Lys Ala Glu Ala Arg Arg Ser Ala
 50                  55                  60

Ala Lys Ile Ala Leu
 65
```

<210> SEQ ID NO 37

<400> SEQUENCE: 37

000

<210> SEQ ID NO 38
<211> LENGTH: 69
<212> TYPE: PRT
<213> ORGANISM: Drosophila melanogaster

<400> SEQUENCE: 38

Val Glu Ala Leu Gln Glu Phe Trp Gln Met Lys Gln Ser Arg Gly Ala
1               5                   10                  15

Glu Leu Lys Asn Gly Ala Leu Val Ile Tyr Glu Ser Ile Pro Ser Asn
            20                  25                  30

Ser Gln Pro Tyr Ile Cys Phe Val Thr Leu Pro Gly Gly Ser Cys Phe
        35                  40                  45

Gly Ser Phe Gln Asn Cys Pro Thr Lys Ala Glu Ala Arg Arg Ser Ser
    50                  55                  60

Ala Lys Ile Ala Leu
65

<210> SEQ ID NO 39
<211> LENGTH: 69
<212> TYPE: PRT
<213> ORGANISM: Enterobacter cloacae

<400> SEQUENCE: 39

Leu Gln Ala Leu Leu Pro Ala Ser Pro Cys Ser Ala Glu Ile Thr Ala
1               5                   10                  15

Glu Ala Glu Arg Leu Thr Leu Arg Asn Gly Asn Ile Leu Ala Thr Leu
            20                  25                  30

Asn Leu Lys Gly Gln Leu Ala Phe Tyr Asn Ala Arg Gly Glu Leu Leu
        35                  40                  45

Leu Glu Glu Met Trp Arg Gln Arg Ser Thr Val Gly Ile Gly Ala Ser
    50                  55                  60

Glu Lys Ser Gln Asp
65

<210> SEQ ID NO 40
<211> LENGTH: 130
<212> TYPE: PRT
<213> ORGANISM: Homo sapiens

<400> SEQUENCE: 40

Glu Val Cys Ile Leu His Glu Tyr Met Gln Arg Val Leu Lys Val Arg
1               5                   10                  15

Pro Val Tyr Asn Phe Phe Glu Cys Glu Asn Pro Ser Glu Pro Phe Gly
            20                  25                  30

Ala Ser Val Thr Ile Asp Gly Val Thr Tyr Gly Ser Gly Thr Ala Ser
        35                  40                  45

Ser Lys Lys Leu Ala Lys Asn Lys Ala Ala Arg Ala Thr Leu Glu Ile
    50                  55                  60

Leu Pro Tyr Gln Ile Leu His Glu Cys Leu Lys Arg Asn His Gly Met
65                  70                  75                  80

Gly Asp Thr Ser Ile Lys Phe Glu Val Val Pro Gly Lys Asn Gln Lys
            85                  90                  95

Ser Glu Tyr Val Met Ala Cys Gly Lys His Thr Val Arg Gly Trp Cys
        100                 105                 110

Lys Asn Lys Arg Val Gly Lys Gln Leu Ala Ser Gln Lys Ile Leu Gln
    115                 120                 125

Leu Leu
    130

<210> SEQ ID NO 41
<211> LENGTH: 131
<212> TYPE: PRT
<213> ORGANISM: Mus musculus

<400> SEQUENCE: 41

Ile Gln Cys Ile Pro Leu Pro Trp Gln Cys Asp Gly Trp Pro Thr Cys
1               5                   10                  15

Glu Asp Lys Ser Asp Glu Ala Asp Cys Pro Val Thr Gly Glu Ala Arg
            20                  25                  30

Pro Tyr Gly Lys Glu Thr Val Asp Leu Arg Gln Gly Arg Ala Arg Gly
        35                  40                  45

Gly Asp Pro Thr His Phe His Thr Val Asn Val Ala Gln Pro Val Arg
    50                  55                  60

Phe Ser Leu Ala Thr Phe Ser Thr Asp Gln Glu Leu Arg Phe Val Leu
65                  70                  75                  80

Ala Gln Glu Trp Asp Gln Pro Glu Arg Ser Phe Gly Trp Lys Asp Gln
                85                  90                  95

Arg Lys Leu Trp Val Gly Tyr Gln Tyr Val Ile Thr Gly Arg Asn His
            100                 105                 110

Ser Leu Glu Gly Arg Trp Glu Val Ala Phe Lys Gly Ser Pro Glu Val
        115                 120                 125

Phe Leu Pro
    130

<210> SEQ ID NO 42
<211> LENGTH: 125
<212> TYPE: PRT
<213> ORGANISM: Drosophila melanogaster

<400> SEQUENCE: 42

Phe Val Cys Ile Leu His Glu Tyr Val Gln His Ala Leu Lys Thr Gln
1               5                   10                  15

Pro Thr Tyr Glu Phe Lys Glu Leu Gln Asn Ala Ala Thr Pro Tyr Ser
            20                  25                  30

Ala Thr Val Ser Val Asn Asn Leu Lys Tyr Gly Thr Gly Tyr Gly Thr
        35                  40                  45

Ser Lys Lys Gln Ala Lys Ser Glu Ala Ala Arg Glu Thr Leu Glu Ile
    50                  55                  60

Leu Ile Pro Asn Ala Ile Leu Leu Thr Cys Leu Gln Arg Asn Tyr Gly
65                  70                  75                  80

Ser Asp Val Gln Ile Ser Gln Glu Ile Asn Arg Thr Ala Asn Asn Lys
                85                  90                  95

Asn Glu Phe Thr Met Thr Val Gly Lys His Thr Ala Lys Val Val Cys
            100                 105                 110

Lys Asn Lys Arg Glu Gly Lys Gln Leu Ala Ser Gln Ala
        115                 120                 125

<210> SEQ ID NO 43
<211> LENGTH: 131
<212> TYPE: PRT
<213> ORGANISM: Anopheles gambiae

<400> SEQUENCE: 43

Thr Val Thr Glu Asn Leu Lys Ala Gln Ser Leu Thr Ser Asp Ala Val

```
                 1               5                  10                 15
Val Glu Tyr Cys Lys Lys Leu Phe Arg Phe Lys Thr Ile Arg Val Leu
             20                  25                 30

Arg Phe Lys Ser Trp Ala Ala Arg Lys Phe Thr Lys His Arg Lys
             35                  40                 45

His Ile Lys Asn Leu Gln Arg Pro Thr Leu Pro Asp Gly Thr Lys Leu
 50                  55                  60

Ile Thr Ile Asn Glu Leu Lys Tyr Gly Thr Gly Tyr Gly Thr Ser Lys
 65                  70                  75                  80

Lys Gln Ala Lys Ser Glu Ala Ala Arg Glu Thr Leu Glu Ile Leu Ile
             85                  90                 95

Pro Asp Met Lys Asp Lys Ile Thr Gly Lys Asp Ala Lys Gly Ala Ser
            100                 105                110

Asn Gly Gly Gly Ala Gly Ala Gly Gly Ser Gly Ser Gly Gly Ser Gln
            115                 120                125

Gln Gln Ser
        130
```

<210> SEQ ID NO 44
<211> LENGTH: 76
<212> TYPE: PRT
<213> ORGANISM: Homo sapiens

<400> SEQUENCE: 44

```
Asn His Gly Glu Leu Leu Asn Ala Ala Ile Glu Ala Leu Lys Ala Thr
 1               5                  10                 15

Leu Asp Val Phe Phe Val Pro Leu Lys Glu Leu Ala Asp Leu Pro Gln
             20                  25                 30

Asn Lys Ser Ser Gln Glu Ser Ile Val Cys Glu Leu Arg Cys Lys Ser
             35                  40                 45

Val Tyr Leu Gly Thr Gly Cys Gly Lys Ser Lys Glu Asn Ala Lys Ala
 50                  55                  60

Val Ala Ser Arg Glu Ala Leu Lys Leu Phe Leu Lys
 65                  70                  75
```

<210> SEQ ID NO 45
<211> LENGTH: 56
<212> TYPE: PRT
<213> ORGANISM: Mus musculus

<400> SEQUENCE: 45

```
Asn His Gly Glu Leu Leu Asn Ala Ala Ile Glu Ala Leu Lys Ala Thr
 1               5                  10                 15

Leu Asp Val Phe Phe Val Pro Leu Lys Glu Leu Ala Asp Leu Pro Gln
             20                  25                 30

Asn Lys Ser Ser Gln Glu Ser Ile Val Cys Glu Leu Arg Cys Lys Ser
             35                  40                 45

Val Tyr Leu Gly Thr Gly Cys Gly
 50                  55
```

<210> SEQ ID NO 46
<211> LENGTH: 71
<212> TYPE: PRT
<213> ORGANISM: Homo sapiens

<400> SEQUENCE: 46

```
Asn Pro Met Gly Leu Leu Val Glu Glu Leu Lys Lys Arg Asn Val Ser
 1               5                  10                 15
```

```
Ala Pro Glu Ser Arg Leu Thr Arg Gln Ser Gly Gly Thr Thr Ala Leu
            20                  25                  30

Pro Leu Tyr Phe Val Gly Leu Tyr Cys Asp Lys Lys Leu Ile Ala Glu
        35                  40                  45

Gly Pro Gly Glu Thr Val Leu Val Ala Glu Glu Ala Ala Arg Val
50                  55                  60

Ala Leu Arg Lys Leu Tyr Gly
65                  70

<210> SEQ ID NO 47
<211> LENGTH: 71
<212> TYPE: PRT
<213> ORGANISM: Mus musculus

<400> SEQUENCE: 47

Asn Pro Met Gly Leu Leu Val Glu Glu Leu Lys Lys Arg Asn Ile Ser
1               5                   10                  15

Ala Pro Glu Ser Arg Leu Thr Arg Gln Ser Gly Ser Thr Thr Ala Leu
            20                  25                  30

Pro Leu Tyr Phe Val Gly Leu Tyr Cys Asp Arg Lys Leu Ile Ala Glu
        35                  40                  45

Gly Pro Gly Glu Thr Val Leu Val Ala Glu Glu Ala Ala Arg Val
50                  55                  60

Ala Leu Arg Lys Leu Tyr Gly
65                  70

<210> SEQ ID NO 48
<211> LENGTH: 81
<212> TYPE: PRT
<213> ORGANISM: Drosophila melanogaster

<400> SEQUENCE: 48

Lys Asp Leu Leu Glu Val Trp Thr Pro Gln Glu Pro Ile Gln Leu Leu
1               5                   10                  15

Glu Lys Ile Cys Gln Glu Arg Lys Leu Gly Glu Ala Glu Pro Arg Leu
            20                  25                  30

Leu Gly Asp Cys Gly Lys Asn Thr Val Leu Ala Ala Tyr Gln Val Gly
        35                  40                  45

Ile Tyr Ala Asn Arg Gln Leu Leu Gly Lys Gly Phe Gly Glu Asp Val
        50                  55                  60

Lys Thr Ala Thr Glu Thr Ala Ala Leu Asp Ala Leu Gln Ser Ile Phe
65                  70                  75                  80

Asp

<210> SEQ ID NO 49
<211> LENGTH: 65
<212> TYPE: PRT
<213> ORGANISM: Drosophila melanogaster

<400> SEQUENCE: 49

Asn Met His Pro Cys Met Val Leu Met Gln Met Arg Pro Gln Thr Thr
1               5                   10                  15

Phe Lys Phe Leu Gly Ser Ser Gly Glu Asn Arg Lys Val Phe Ser Met
            20                  25                  30

Gly Val Ser Val Asp Asn Cys Glu Phe Lys Ala Asp Gly Pro Thr Lys
        35                  40                  45

Lys Asp Ala Arg Arg Lys Val Ala Ala Leu Val Cys Asn Lys Leu Phe
```

Gly
65

<210> SEQ ID NO 50
<211> LENGTH: 127
<212> TYPE: PRT
<213> ORGANISM: Drosophila melanogaster

<400> SEQUENCE: 50

Ser Lys Asp Ala Leu Met Val Leu Asn Glu Leu Lys Gly Val Thr Val
1               5                   10                  15

Asp Asn Met Gln Ile Lys Arg Asp His Glu Gly Lys Ile Met Ala Arg
            20                  25                  30

Val Val Val Asn Ser Lys Lys Tyr Glu Ala Glu Gly Ser Ser Val Asn
        35                  40                  45

Ser Ala Arg Asn Ala Ala Cys Glu Lys Ala Leu Gln Glu Ile Leu Asn
    50                  55                  60

Met His Pro Cys Met Val Leu Asn Tyr Met Arg Pro Gln Cys Thr Phe
65                  70                  75                  80

Ile Val Ser Gly Gly Thr Gly Thr Asn Gln Asn Asn Thr Phe Ser Met
                85                  90                  95

Ser Val Cys Val Asp Asn Cys Glu Phe Asn Ala Glu Gly Pro Ser Lys
            100                 105                 110

Lys Ala Ala Arg Tyr Lys Leu Ser Ala Leu Val Cys Asn Lys Leu
        115                 120                 125

<210> SEQ ID NO 51
<211> LENGTH: 62
<212> TYPE: PRT
<213> ORGANISM: Drosophila melanogaster

<400> SEQUENCE: 51

Pro Lys Asn Ala Leu Met Ala Leu Asn Glu Val Lys Gly Val Thr Ile
1               5                   10                  15

Ser Asp Phe Thr Ile Asp Ser Asn Thr Asp Gly Gly Phe Thr Ala Val
            20                  25                  30

Val Thr Val Asn Ser Asn Gln Tyr Glu Gly Lys Gly Thr Ser Lys Met
        35                  40                  45

Thr Ala Lys Asn Ala Ala Cys Glu Lys Ala Trp Arg Asp Phe
    50                  55                  60

<210> SEQ ID NO 52
<211> LENGTH: 113
<212> TYPE: PRT
<213> ORGANISM: Anopheles gambiae

<400> SEQUENCE: 52

Ile Ala Lys Arg Gln Ala Ala Gln Arg Met Trp Gln Arg Leu Gln Asp
1               5                   10                  15

Gln Pro Leu Glu Pro Ser Gln Ile Met Gln Leu Leu Asp Glu Glu Gly
            20                  25                  30

Asn Glu Glu Thr Gly Tyr Ala Gly Arg Tyr Ala Gly Leu Lys Asp Val
        35                  40                  45

Cys Ile Pro Thr Leu Thr Thr Ser Gln Ser His Lys Val Ser Gln Phe
    50                  55                  60

His Lys Ala Leu Ile Asp Lys Leu Thr Gly Ser Ile Phe Leu Asp His
65                  70                  75                  80

```
Pro Ala Val Tyr Met Asn Val His Lys Pro Asp Thr Gln Phe His Ser
                85                  90                  95
Cys Arg Val Val Asn Val His Thr Asn Asn Val Asn Gly Glu Glu
            100                 105                 110
Glu

<210> SEQ ID NO 53
<211> LENGTH: 110
<212> TYPE: PRT
<213> ORGANISM: Caenorhabditis elegans

<400> SEQUENCE: 53

Thr Thr Val Ala Val Leu Asn Glu Phe Val Gln Arg Leu Ala Lys Gly
1               5                   10                  15
Thr Leu Leu Tyr Glu Ile Glu Asp Thr Arg Asn Ile His Cys Pro Tyr
                20                  25                  30
Lys Ala Thr Ala Leu Leu Thr Met Lys Met Cys Thr Leu Arg Glu Met
            35                  40                  45
Ala Gly Gln Cys Lys Glu Ser Leu Val Val Leu Ser Glu Ile Ala Ala
        50                  55                  60
Asn Asp Glu Asn Ser Thr Thr Tyr Ser Gln Gly Leu Leu Pro Asp Leu
65                  70                  75                  80
Arg Arg Phe Pro Val Gly Ser Gly Val Gly Ala Asn Lys Lys Thr Ala
                85                  90                  95
Arg Leu Val Ala Ala Arg Asp Ala Leu Leu Lys Leu Ile Pro
            100                 105                 110

<210> SEQ ID NO 54
<211> LENGTH: 60
<212> TYPE: PRT
<213> ORGANISM: Oryza sativa

<400> SEQUENCE: 54

Pro Lys Ser Leu Leu Gln Thr Leu Leu Met Arg Ala Gly His Thr Pro
1               5                   10                  15
Pro Lys Tyr Lys Thr Lys His Leu Lys Thr Asn Glu Phe Arg Ala Ile
                20                  25                  30
Val Glu Phe Lys Gly Met Gln Phe Ala Gly Lys Pro Lys Arg Asn Lys
            35                  40                  45
Gln Leu Ala Glu Arg Asp Ala Ala Ile Glu Ala Leu
        50                  55                  60

<210> SEQ ID NO 55
<211> LENGTH: 63
<212> TYPE: PRT
<213> ORGANISM: Oryza sativa

<400> SEQUENCE: 55

Ala Lys Asn Gln Leu Gln Thr Leu Leu Thr Arg Ala Gly His Asp Asn
1               5                   10                  15
Pro Ser Tyr Lys Thr Lys Gln Ile Lys Asn Ser Leu Phe Arg Ser Thr
                20                  25                  30
Val Glu Phe Asn Gly Met Gln Phe Val Gly Gln Pro Cys Ala Asn Lys
            35                  40                  45
Lys Leu Ala Glu Lys Asp Ala Ala Gly Glu Ala Leu Asn Trp Leu
        50                  55                  60
```

```
<210> SEQ ID NO 56
<211> LENGTH: 129
<212> TYPE: PRT
<213> ORGANISM: Arabidopsis thaliana

<400> SEQUENCE: 56

Met Ala Phe Gln Ser Gln Arg Gln Leu Pro Ser Asp Met Val His Arg
1               5                   10                  15

Asp Glu Leu His Ala Gln Val Glu Ile Asp Gly Arg Val Val Gly Glu
            20                  25                  30

Gly Val Gly Ser Thr Trp Asp Glu Ala Arg Met Gln Ala Ala Glu Arg
        35                  40                  45

Ala Leu Ser Ser Val Arg Ser Met Leu Gly Gln Pro Leu His Lys Arg
    50                  55                  60

Gln Gly Ser Pro Tyr Lys Pro Ser Leu Val Ser Ser Thr Asp Leu Arg
65                  70                  75                  80

Phe Ser Val Glu Ala Trp Leu Ser Asn Gln Lys Ile Gly Gly Gly Ile
                85                  90                  95

Gly Lys Ser Arg Arg Glu Ala Leu His Lys Ala Ala Glu Ala Ser Ile
            100                 105                 110

Gln Asn Leu Ala Asp Gly Tyr Met Arg Ala Asn Gly Asp Pro Gly Pro
        115                 120                 125

Ser

<210> SEQ ID NO 57
<211> LENGTH: 63
<212> TYPE: PRT
<213> ORGANISM: Arabidopsis thaliana

<400> SEQUENCE: 57

Ser Ala Leu Gln Glu Ile Gly Arg Arg Cys Gly Ser Lys Val Glu Phe
1               5                   10                  15

Arg Thr Val Ile Ser Thr Asn Lys Glu Leu Gln Phe Ser Val Glu Val
            20                  25                  30

Leu Phe Thr Gly Glu Lys Ile Gly Ile Gly Met Ala Lys Thr Lys Lys
        35                  40                  45

Asp Ala His Gln Gln Ala Ala Glu Asn Ala Leu Arg Ser Leu Ala
    50                  55                  60

<210> SEQ ID NO 58
<211> LENGTH: 73
<212> TYPE: PRT
<213> ORGANISM: Dictyostelium discoideum

<400> SEQUENCE: 58

Lys Asn Asp Leu Gln Thr Tyr Ile Gln Gln Lys Arg Ile Gly Tyr Leu
1               5                   10                  15

Pro Val Tyr His Ser Glu Cys Arg Gly Pro Asp His Glu Arg Glu Tyr
            20                  25                  30

Arg Thr His Ile Arg Val Gly Glu Ile Asn Ser Lys His Asn Asn Lys
        35                  40                  45

Ile Val Tyr Ser Asp Trp Tyr Lys Asn Lys Thr Ala Glu Ser Cys
    50                  55                  60

Cys Ala Ile Lys Val Leu Asn Tyr Leu
65                  70

<210> SEQ ID NO 59
<211> LENGTH: 139
```

```
<212> TYPE: PRT
<213> ORGANISM: Oryza sativa

<400> SEQUENCE: 59

Tyr Lys Ser Arg Leu Gln Glu Leu Cys Gln Gln Arg Trp Ala Pro
1               5                   10                  15

Pro Glu Tyr Thr His Arg Cys Ala Gly Pro Ala His Ala Pro Leu Phe
            20                  25                  30

Gly Ala Thr Val Ser Val Asn Gly Val Glu Phe Tyr Lys Ser Gln Leu
        35                  40                  45

Gln Ile Tyr Ala Gln Lys Lys Gly Lys Leu Leu Pro Ser Tyr Gln Thr
    50                  55                  60

Ile Arg Glu Gly Pro Gly His Ala Ser Arg Phe Lys Ser Val Val Thr
65                  70                  75                  80

Val Asp Gly Lys Ala Phe Tyr Lys Asn Leu Leu Gln Glu Leu Ala Gln
                85                  90                  95

Lys His Gly Phe Ser Leu Pro Val Tyr Ser Thr Thr Ser Asp Gly Ser
            100                 105                 110

Val Gln Asp Gly Ser Phe Gln Gly Glu Pro Ala Asn Thr Lys Lys Gln
        115                 120                 125

Ala Glu Met Asn Ala Ala Arg Val Ala Phe Gln
    130                 135

<210> SEQ ID NO 60
<211> LENGTH: 134
<212> TYPE: PRT
<213> ORGANISM: Arabidopsis thaliana

<400> SEQUENCE: 60

Tyr Lys Gly Gln Leu Gln Ala Tyr Ala Leu Gln His Asn Leu Glu Leu
1               5                   10                  15

Pro Val Tyr Ala Asn Glu Arg Glu Gly Pro Pro His Ala Pro Arg Phe
            20                  25                  30

Arg Cys Asn Val Thr Phe Cys Gly Gln Thr Phe Gln Ser Ser Glu Phe
        35                  40                  45

Phe Pro Thr Leu Lys Ser Ala Glu His Ala Ala Ala Lys Ile Ala Val
    50                  55                  60

Ala Ser Leu Tyr Lys Asn Leu Leu Gln Glu Ile Ala Gln Lys Glu Ser
65                  70                  75                  80

Ser Leu Leu Pro Phe Tyr Ala Thr Ala Thr Ser Gly Pro Ser His Ala
                85                  90                  95

Pro Thr Phe Thr Ser Thr Val Glu Phe Ala Gly Lys Val Phe Ser Gly
            100                 105                 110

Glu Glu Ala Lys Thr Lys Lys Leu Ala Glu Met Ser Ala Ala Lys Val
        115                 120                 125

Ala Phe Met Ser Ile Lys
    130

<210> SEQ ID NO 61
<211> LENGTH: 134
<212> TYPE: PRT
<213> ORGANISM: Arabidopsis thaliana

<400> SEQUENCE: 61

Tyr Lys Asn Gln Leu Gln Glu Leu Ala Gln Arg Ser Cys Phe Asn Leu
1               5                   10                  15

Pro Ser Tyr Thr Cys Ile Arg Glu Gly Pro Asp His Ala Pro Arg Phe
```

```
            20                  25                  30
Lys Ala Ser Val Asn Phe Asn Gly Glu Ile Phe Glu Ser Pro Thr Tyr
        35                  40                  45

Cys Ser Thr Leu Arg Gln Ala Glu His Ala Ala Ala Glu Val Ser Leu
    50                  55                  60

Asn Val Leu Tyr Lys Asn Leu Leu Gln Glu Thr Ala His Arg Ala Gly
65                  70                  75                  80

Leu Asp Leu Pro Met Tyr Thr Ser Val Arg Ser Gly Ser Cys His Phe
                85                  90                  95

Pro Gly Phe Ser Cys Thr Val Glu Leu Ala Gly Met Thr Phe Thr Gly
            100                 105                 110

Glu Ser Ala Lys Thr Lys Lys Gln Ala Glu Lys Asn Ala Ala Ile Ala
        115                 120                 125

Ala Trp Ser Ser Leu Lys
    130

<210> SEQ ID NO 62
<211> LENGTH: 110
<212> TYPE: PRT
<213> ORGANISM: Arabidopsis thaliana

<400> SEQUENCE: 62

Tyr Lys Asn Gln Leu Gln Glu Leu Ala Gln Arg Ser Cys Phe Ser Leu
1               5                   10                  15

Pro Ser Tyr Thr Cys Thr Arg Glu Gly Pro Asp His Ala Pro Arg Phe
            20                  25                  30

Lys Ala Ser Val Asn Phe Asn Gly Glu Ile Phe Gly Ile Tyr Lys Asn
        35                  40                  45

Leu Leu Gln Glu Thr Ala His Arg Ala Gly Leu Asp Leu Pro Val Tyr
    50                  55                  60

Thr Ser Val Arg Ser Gly Pro Gly His Ile Pro Thr Phe Ser Cys Thr
65                  70                  75                  80

Val Glu Leu Ala Gly Met Ser Phe Asn Gly Glu Ser Ala Lys Thr Lys
                85                  90                  95

Lys Gln Ala Glu Lys Asn Ala Ala Ile Ala Ala Trp Phe Ser
            100                 105                 110

<210> SEQ ID NO 63
<211> LENGTH: 112
<212> TYPE: PRT
<213> ORGANISM: Arabidopsis thaliana

<400> SEQUENCE: 63

Tyr Lys Asn Gln Leu Gln Glu Leu Ala Gln Arg Ser Cys Phe Asn Leu
1               5                   10                  15

Pro Ser Tyr Thr Cys Ile Arg Glu Gly Pro Asp His Ala Pro Arg Phe
            20                  25                  30

Lys Ala Thr Val Asn Phe Asn Gly Glu Ile Phe Glu Ser Pro Gln Tyr
        35                  40                  45

Cys Ser Thr Leu Arg Gln Ala Glu His Ser Ala Ala Glu Val Ala Leu
    50                  55                  60

Asn Ala Leu Tyr Lys Asn Leu Leu Gln Glu Ile Ala Gln Arg Val Gly
65                  70                  75                  80

Ala Pro Leu Pro Arg Tyr Thr Thr Phe Arg Ser Gly Leu Gly His Gln
                85                  90                  95

Pro Val Phe Thr Gly Thr Val Glu Leu Ala Gly Ile Thr Phe Thr Gly
```

-continued

```
                100                 105                 110
```

<210> SEQ ID NO 64
<211> LENGTH: 88
<212> TYPE: PRT
<213> ORGANISM: Oryza sativa

<400> SEQUENCE: 64

Tyr Lys Asn Gln Leu Gln Glu Leu Ala Gln Arg Ser Cys Phe Asn Leu
1               5                   10                  15

Pro Ala Tyr Thr Cys Leu Arg Glu Gly Pro Asp His Ala Pro Arg Phe
            20                  25                  30

Lys Ala Ala Val Asn Phe Asn Gly Glu Gln Phe Tyr Lys Asn Leu Leu
        35                  40                  45

Gln Glu Val Ala Gln Arg Val Gly Ala Pro Leu Pro Ser Tyr Thr Thr
    50                  55                  60

Glu Arg Ser Gly Leu Gly His Leu Pro Val Phe Thr Cys Thr Val Glu
65                  70                  75                  80

Leu Ala Gly Ile Thr Phe Thr Gly
                85

<210> SEQ ID NO 65
<211> LENGTH: 61
<212> TYPE: PRT
<213> ORGANISM: Arabidopsis thaliana

<400> SEQUENCE: 65

Met Ile Leu Gln Lys Phe Gly Val Lys Ala Ile Tyr Arg Ile Glu Glu
1               5                   10                  15

Val His Val Ser Ser Asn Asp Cys Leu Tyr Arg Cys His Leu Gln Leu
            20                  25                  30

Pro Glu Phe Ser Val Val Ser Asn Val Phe Lys Arg Lys Lys Asp Ser
        35                  40                  45

Glu Gln Ser Ala Ala Glu Leu Ala Leu Glu Lys Leu Gly
    50                  55                  60

<210> SEQ ID NO 66
<211> LENGTH: 65
<212> TYPE: PRT
<213> ORGANISM: Vaccinia virus

<400> SEQUENCE: 66

Pro Val Thr Ile Ile Asn Glu Tyr Cys Gln Ile Thr Lys Arg Asp Trp
1               5                   10                  15

Ser Phe Arg Ile Glu Ser Val Gly Pro Ser Asn Ser Pro Thr Phe Tyr
            20                  25                  30

Ala Cys Val Asp Ile Asp Gly Arg Val Phe Asp Lys Ala Asp Gly Lys
        35                  40                  45

Ser Lys Arg Asp Ala Lys Asn Asn Ala Ala Lys Leu Ala Val Asp Lys
    50                  55                  60

Leu
65

<210> SEQ ID NO 67
<211> LENGTH: 65
<212> TYPE: PRT
<213> ORGANISM: sheeppox virus

<400> SEQUENCE: 67

```
Pro Cys Ser Ala Ile Asn Glu Tyr Cys Gln Phe Thr Ser Arg Asp Trp
1               5                   10                  15

Tyr Ile Asn Ile Ser Ser Cys Gly Asn Gly Arg Lys Pro Met Phe Leu
            20                  25                  30

Ala Ser Val Ile Ile Ser Gly Ile Lys Phe Phe Pro Glu Ile Gly Asn
        35                  40                  45

Thr Lys Lys Glu Ala Lys Gln Lys Ser Thr Lys Arg Thr Ile Asp Phe
    50                  55                  60

Leu
65

<210> SEQ ID NO 68
<211> LENGTH: 65
<212> TYPE: PRT
<213> ORGANISM: lumpy skin disease virus

<400> SEQUENCE: 68

Pro Cys Ser Ala Ile Asn Glu Tyr Cys Gln Phe Thr Ser Arg Asp Trp
1               5                   10                  15

Tyr Ile Asn Ile Ser Ser Cys Gly Asn Gly Arg Lys Pro Met Phe Leu
            20                  25                  30

Ala Ser Val Ile Ile Ser Gly Ile Lys Phe Phe Pro Glu Ile Gly Asn
        35                  40                  45

Thr Lys Lys Glu Ala Lys Gln Lys Ser Thr Lys Arg Thr Ile Asp Phe
    50                  55                  60

Leu
65

<210> SEQ ID NO 69
<211> LENGTH: 66
<212> TYPE: PRT
<213> ORGANISM: Orf virus

<400> SEQUENCE: 69

Pro Val Ser Ala Val Asn Glu Phe Cys Met Met Thr His Arg Pro Leu
1               5                   10                  15

Glu Phe Cys Glu Thr Arg Ala Gly Gly Glu Asp His Cys Pro Arg Phe
            20                  25                  30

Thr Cys Thr Ile Thr Ile Ser Gly Lys Val Val Ala Val Ala Asp Gly
        35                  40                  45

Ala Ser Lys Lys Leu Ala Arg His Thr Ala Cys Ser Ser Ala Leu Thr
    50                  55                  60

Ile Leu
65

<210> SEQ ID NO 70
<211> LENGTH: 64
<212> TYPE: PRT
<213> ORGANISM: Orthoreovirus S1

<400> SEQUENCE: 70

Lys Gly Arg Ala Tyr Arg Lys Glu Leu Val Thr Pro Ala Arg Asp Phe
1               5                   10                  15

Gly His Phe Gly Leu Ser His Tyr Ser Arg Ala Thr Thr Pro Ile Leu
            20                  25                  30

Gly Lys Met Pro Ala Val Phe Ser Gly Met Leu Thr Gly Asn Cys Lys
        35                  40                  45

Met Tyr Pro Phe Ile Lys Gly Thr Ala Lys Leu Lys Thr Val Arg Lys
```

<210> SEQ ID NO 71
<211> LENGTH: 71
<212> TYPE: PRT
<213> ORGANISM: Haemophilus influenzae

<400> SEQUENCE: 71

Ala Lys Thr Arg Leu Gln Glu Tyr Leu Gln Gly Lys His Leu Pro Leu
1               5                   10                  15

Pro Thr Tyr Glu Val Val Asn Ile Gln Gly Glu Ala His Cys Gln Ile
                20                  25                  30

Phe Thr Val Lys Cys Lys Val Lys Ser Ala Glu Lys Ile Asp Arg Thr
            35                  40                  45

Phe Val Ala Lys Gly Ser Ser Arg Arg Lys Ala Glu Gln Ala Ala Ala
        50                  55                  60

Glu Gln Ile Leu Lys Glu Leu
65                  70

<210> SEQ ID NO 72
<211> LENGTH: 66
<212> TYPE: PRT
<213> ORGANISM: Paramecium bursaria Chlorella virus 1

<400> SEQUENCE: 72

Tyr Lys Asp Arg Leu Leu Lys His Thr Arg Lys Val Glu Leu Pro Arg
1               5                   10                  15

Pro Glu Phe Val Ser Val Phe Glu Lys Gly Gly Ala Asn Pro Ser Phe
                20                  25                  30

Ile Val Asp Val Val Ile Asn Gly Gln Lys Ile Ser Thr Gly Thr Gly
            35                  40                  45

Lys Ser Arg Lys Asp Ala Glu Gln Asn Ala Ser Lys Ile Ala Leu His
        50                  55                  60

Thr Met
65

<210> SEQ ID NO 73
<211> LENGTH: 70
<212> TYPE: PRT
<213> ORGANISM: Chilo iridescent virus

<400> SEQUENCE: 73

Ser Ile Gly Phe Leu Asn Glu Phe Cys His Lys Asn Lys Tyr Lys Pro
1               5                   10                  15

Pro Ser Tyr Thr Thr Leu Asn Gln Asn Gly Pro Asp His Ser Pro Thr
                20                  25                  30

Phe Asn Ile Glu Cys Arg Ile Val Asp Tyr Lys Pro Asn Gly Lys Phe
            35                  40                  45

Ile Gly Ser Gly Leu Ser Met Lys Glu Ala Lys Lys Asn Ala Ala Phe
        50                  55                  60

Lys Thr Ile Lys Glu Leu
65              70

<210> SEQ ID NO 74
<211> LENGTH: 69
<212> TYPE: PRT
<213> ORGANISM: Kadipiro virus

<400> SEQUENCE: 74

```
Asn Val Lys Gly Met Leu Gln Glu Leu Cys Val Lys Arg Gly Leu Glu
1               5                   10                  15

Leu Pro Val Tyr Glu Lys Leu Ser Lys Val Gly Pro Asp His Ala Pro
            20                  25                  30

Thr Ile Thr Val Lys Leu Thr Ala Asn Gly Ile Glu Val Ile Glu Ala
                35                  40                  45

Ala Ser Ser Arg Ala Gln Ala Glu Lys Leu Ala Ala Ala Thr Leu Tyr
        50                  55                  60

Glu Lys Met Lys His
65

<210> SEQ ID NO 75
<211> LENGTH: 68
<212> TYPE: PRT
<213> ORGANISM: Banna virus

<400> SEQUENCE: 75

Asp Pro Val Ser Val Val His Ser Phe Ala Arg Ser Gln Gly Leu Pro
1               5                   10                  15

Leu Asp Phe Glu Thr Val Gly Cys Glu Gly Pro Ser His Asp Pro Arg
            20                  25                  30

Phe Val Ile Glu Cys Lys Phe Leu Asp Phe Gln His Gln Cys Thr Asp
                35                  40                  45

Ser Ser Lys Lys Arg Ala Ile Gln Lys Ile Cys Val Leu Ile Ser Asn
        50                  55                  60

Asp Leu Lys Glu
65

<210> SEQ ID NO 76
<211> LENGTH: 68
<212> TYPE: PRT
<213> ORGANISM: Drosophila C virus

<400> SEQUENCE: 76

Asp Lys Ile Ser Thr Leu Lys Met Val Ala Asp Tyr Tyr Gln Lys Glu
1               5                   10                  15

Val Lys Tyr Asp Phe Asp Ala Val Glu Ser Pro Arg Glu Ala Pro Val
            20                  25                  30

Phe Arg Cys Thr Cys Arg Phe Leu Gly Tyr Thr Ile Met Thr Gln Gly
                35                  40                  45

Ile Gly Lys Lys Asn Pro Lys Gln Glu Ala Ala Arg Gln Met Leu Leu
        50                  55                  60

Leu Leu Ser Gly
65

<210> SEQ ID NO 77
<211> LENGTH: 65
<212> TYPE: PRT
<213> ORGANISM: Acyrthosiphon pisum

<400> SEQUENCE: 77

Pro Ile Ser Ala Cys Leu Glu Leu Ile Ser Lys Leu Lys Thr Ala Gly
1               5                   10                  15

Pro Val Glu His Phe Glu Arg Ala Gly Pro His Ser Pro Thr Tyr
            20                  25                  30

Ser Cys Thr Val Thr Tyr Ala Gly Arg His Phe Gly Gly Glu Gly Pro
                35                  40                  45

Ser Lys Ala Ser Ala Lys Thr Gln Ala Tyr Gly Ala Leu Arg Gln Tyr
```

-continued

```
                 50                  55                  60
Leu
 65

<210> SEQ ID NO 78
<211> LENGTH: 17
<212> TYPE: PRT
<213> ORGANISM: Porcine rotavirus

<400> SEQUENCE: 78

Ser Lys Lys Glu Ala Lys Arg Ile Ala Ala Lys Asp Ile Leu Asp Gln
 1               5                  10                  15

Ile

<210> SEQ ID NO 79
<211> LENGTH: 68
<212> TYPE: PRT
<213> ORGANISM: Bovine rotavirus Shintoku strain

<400> SEQUENCE: 79

Asn Ala Leu Val Lys Leu Asn Asp Cys Ile Thr Lys Tyr Asn Leu Lys
 1               5                  10                  15

Ile Ile Cys Thr Phe Asp Val Asn Leu Asp Asp Gly Ser Ile Met
                 20                  25                  30

Tyr Ile Cys Tyr Leu Lys Val Gly Ser Ala Glu Ala Thr Gly Asn Gly
             35                  40                  45

Cys Ser Lys Lys Glu Ala Lys Arg Ala Ala Val Ser Ile Leu Asp
         50                  55                  60

Gln Leu Gly Met
 65

<210> SEQ ID NO 80
<211> LENGTH: 62
<212> TYPE: PRT
<213> ORGANISM: Human rotavirus C

<400> SEQUENCE: 80

Leu Asn Asp Tyr Ile Thr Lys Tyr Gln Leu Lys Leu Glu Cys Thr Phe
 1               5                  10                  15

Asp Ile Phe Le

```
Gly Arg Glu Phe Pro Glu Gly Glu Gly Arg Ser Lys Lys Glu Ala Lys
 50                  55                  60

Asn Ala Ala Ala Lys Leu Ala Val Glu Ile Leu Asn Lys Glu Lys Lys
 65                  70                  75                  80

Ala Val Ser Pro Leu Leu Leu Thr Thr Thr Asn Ser Ser Glu Gly Leu
                 85                  90                  95

Ser Met Gly Asn Tyr Ile Gly Leu Ile Asn Arg Ile Ala Gln Lys Lys
                100                 105                 110

Arg Leu Thr Val Asn Tyr Glu Gln Cys Ala Ser Gly Val His Gly Pro
            115                 120                 125

Glu Gly Phe His Tyr Lys Cys Lys Met Gly Gln Lys Glu Tyr Ser Ile
        130                 135                 140

Gly Thr Gly Ser Thr Lys Gln Glu Ala Lys Gln Leu Ala Ala Lys Leu
145                 150                 155                 160

Ala Tyr Leu Gln Ile Leu Ser Glu Glu Thr Ser Val Lys Ser Asp Tyr
                165                 170                 175

Leu Ser Ser Gly Ser Phe Ala Thr Thr Cys Glu Ser Gln Ser Asn Ser
            180                 185                 190

Leu Val Thr Ser Thr Leu Ala Ser Glu Ser Ser Glu Gly Asp Phe
        195                 200                 205

Ser Ala Asp Thr Ser Glu Ile Asn Ser Asn Ser Asp Ser Leu Asn Ser
210                 215                 220

Ser Ser Leu Leu Met Asn Gly Leu Arg Asn Asn Gln Arg Lys Ala Lys
225                 230                 235                 240

Arg Ser Leu Ala Pro Arg Phe Asp Leu Pro Asp Met Lys Glu Thr Lys
                245                 250                 255

Tyr Thr Val Asp Lys Arg Phe Gly Met Asp Phe Lys Glu Ile Glu Leu
            260                 265                 270

Ile Gly Ser Gly Gly Phe Gly Gln Val Phe Lys Ala Lys His Arg Ile
        275                 280                 285

Asp Gly Lys Thr Tyr Val Ile Lys Arg Val Lys Tyr Asn Asn Glu Lys
    290                 295                 300

Ala Glu Arg Glu Val Lys Ala Leu Ala Lys Leu Asp His Val Asn Ile
305                 310                 315                 320

Val His Tyr Asn Gly Cys Trp Asp Gly Phe Asp Tyr Asp Pro Glu Thr
                325                 330                 335

Ser Asp Asp Ser Leu Glu Ser Ser Asp Tyr Asp Pro Glu Asn Ser Lys
            340                 345                 350

Asn Ser Ser Arg Ser Lys Thr Lys Cys Leu Phe Ile Gln Met Glu Phe
        355                 360                 365

Cys Asp Lys Gly Thr Leu Glu Gln Trp Ile Glu Lys Arg Arg Gly Glu
    370                 375                 380

Lys Leu Asp Lys Val Leu Ala Leu Glu Leu Phe Glu Gln Ile Thr Lys
385                 390                 395                 400

Gly Val Asp Tyr Ile His Ser Lys Lys Leu Ile His Arg Asp Leu Lys
                405                 410                 415

Pro Ser Asn Ile Phe Leu Val Asp Thr Lys Gln Val Lys Ile Gly Asp
            420                 425                 430

Phe Gly Leu Val Thr Ser Leu Lys Asn Asp Gly Lys Arg Thr Arg Ser
        435                 440                 445

Lys Gly Thr Leu Arg Tyr Met Ser Pro Glu Gln Ile Ser Ser Gln Asp
    450                 455                 460
```

```
Tyr Gly Lys Glu Val Asp Leu Tyr Ala Leu Gly Leu Ile Leu Ala Glu
465                 470                 475                 480

Leu Leu His Val Cys Asp Thr Ala Phe Glu Thr Ser Lys Phe Phe Thr
            485                 490                 495

Asp Leu Arg Asp Gly Ile Ile Ser Asp Ile Phe Asp Lys Lys Glu Lys
            500                 505                 510

Thr Leu Gln Lys Leu Leu Ser Lys Lys Pro Glu Asp Arg Pro Asn
        515                 520                 525

Thr Ser Glu Ile Leu Arg Thr Leu Thr Val Trp Lys Lys Ser Pro Glu
    530                 535                 540

Lys Asn Glu Arg His Thr Cys
545                 550
```

<210> SEQ ID NO 82
<211> LENGTH: 172
<212> TYPE: PRT
<213> ORGANISM: Artificial Sequence
<220> FEATURE:
<223> OTHER INFORMATION: Synthetic

<400> SEQUENCE: 82

```
Met Ala Gly Asp Leu Ser Ala Gly Phe Phe Met Glu Glu Leu Asn Thr
1               5                   10                  15

Tyr Arg Gln Lys Gln Gly Val Val Leu Lys Tyr Gln Glu Leu Pro Asn
            20                  25                  30

Ser Gly Pro Pro His Asp Arg Arg Phe Thr Phe Gln Val Ile Ile Asp
        35                  40                  45

Gly Arg Glu Phe Pro Glu Gly Glu Gly Arg Ser Lys Lys Glu Ala Lys
    50                  55                  60

Asn Ala Ala Ala Lys Leu Ala Val Glu Ile Leu Asn Lys Glu Lys Lys
65                  70                  75                  80

Ala Val Ser Pro Leu Leu Leu Thr Thr Thr Asn Ser Ser Glu Gly Leu
                85                  90                  95

Ser Met Gly Asn Tyr Ile Gly Leu Ile Asn Arg Ile Ala Gln Lys Lys
            100                 105                 110

Arg Leu Thr Val Asn Tyr Glu Gln Cys Ala Ser Gly Val His Gly Pro
        115                 120                 125

Glu Gly Phe His Tyr Lys Cys Lys Met Gly Gln Lys Glu Tyr Ser Ile
    130                 135                 140

Gly Thr Gly Ser Thr Lys Gln Glu Ala Lys Gln Leu Ala Ala Lys Leu
145                 150                 155                 160

Ala Tyr Leu Gln Ile Leu Ser Glu Glu Thr Ser Val
                165                 170
```

<210> SEQ ID NO 83
<211> LENGTH: 90
<212> TYPE: PRT
<213> ORGANISM: Artificial Sequence
<220> FEATURE:
<223> OTHER INFORMATION: Synthetic

<400> SEQUENCE: 83

```
Lys Ser Asp Tyr Leu Ser Ser Gly Ser Phe Ala Thr Thr Cys Glu Ser
1               5                   10                  15

Gln Ser Asn Ser Leu Val Thr Ser Thr Leu Ala Ser Glu Ser Ser Ser
            20                  25                  30

Glu Gly Asp Phe Ser Ala Asp Thr Ser Glu Ile Asn Ser Asn Ser Asp
        35                  40                  45
```

Ser Leu Asn Ser Ser Leu Leu Met Asn Gly Leu Arg Asn Asn Gln
         50                  55                  60

Arg Lys Ala Lys Arg Ser Leu Ala Pro Arg Phe Asp Leu Pro Asp Met
 65                  70                  75                  80

Lys Glu Thr Lys Tyr Thr Val Asp Lys Arg
                 85                  90

<210> SEQ ID NO 84
<211> LENGTH: 289
<212> TYPE: PRT
<213> ORGANISM: Artificial Sequence
<220> FEATURE:
<223> OTHER INFORMATION: Synthetic

<400> SEQUENCE: 84

Phe Gly Met Asp Phe Lys Glu Ile Glu Leu Ile Gly Ser Gly Gly Phe
 1               5                  10                  15

Gly Gln Val Phe Lys Ala Lys His Arg Ile Asp Gly Lys Thr Tyr Val
             20                  25                  30

Ile Lys Arg Val Lys Tyr Asn Asn Glu Lys Ala Glu Arg Glu Val Lys
         35                  40                  45

Ala Leu Ala Lys Leu Asp His Val Asn Ile Val His Tyr Asn Gly Cys
     50                  55                  60

Trp Asp Gly Phe Asp Tyr Asp Pro Glu Thr Ser Asp Ser Leu Glu
 65                  70                  75                  80

Ser Ser Asp Tyr Asp Pro Glu Asn Ser Lys Asn Ser Ser Arg Ser Lys
                 85                  90                  95

Thr Lys Cys Leu Phe Ile Gln Met Glu Phe Cys Asp Lys Gly Thr Leu
            100                 105                 110

Glu Gln Trp Ile Glu Lys Arg Arg Gly Glu Lys Leu Asp Lys Val Leu
            115                 120                 125

Ala Leu Glu Leu Phe Glu Gln Ile Thr Lys Gly Val Asp Tyr Ile His
        130                 135                 140

Ser Lys Lys Leu Ile His Arg Asp Leu Lys Pro Ser Asn Ile Phe Leu
145                 150                 155                 160

Val Asp Thr Lys Gln Val Lys Ile Gly Asp Phe Gly Leu Val Thr Ser
                165                 170                 175

Leu Lys Asn Asp Gly Lys Arg Thr Arg Ser Lys Gly Thr Leu Arg Tyr
            180                 185                 190

Met Ser Pro Glu Gln Ile Ser Ser Gln Asp Tyr Gly Lys Glu Val Asp
            195                 200                 205

Leu Tyr Ala Leu Gly Leu Ile Leu Ala Glu Leu Leu His Val Cys Asp
        210                 215                 220

Thr Ala Phe Glu Thr Ser Lys Phe Phe Thr Asp Leu Arg Asp Gly Ile
225                 230                 235                 240

Ile Ser Asp Ile Phe Asp Lys Lys Glu Lys Thr Leu Leu Gln Lys Leu
                245                 250                 255

Leu Ser Lys Lys Pro Glu Asp Arg Pro Asn Thr Ser Glu Ile Leu Arg
            260                 265                 270

Thr Leu Thr Val Trp Lys Lys Ser Pro Glu Lys Asn Glu Arg His Thr
        275                 280                 285

Cys

<210> SEQ ID NO 85
<211> LENGTH: 39

```
<212> TYPE: DNA
<213> ORGANISM: Artificial Sequence
<220> FEATURE:
<223> OTHER INFORMATION: Synthetic

<400> SEQUENCE: 85
gggaggacga tgcggatcag ccatgtttac gtcactcct                    39

<210> SEQ ID NO 86
<211> LENGTH: 70
<212> TYPE: RNA
<213> ORGANISM: Artificial Sequence
<220> FEATURE:
<223> OTHER INFORMATION: Synthetic

<400> SEQUENCE: 86
gggaggacga ugcggaccga aaaagaccug acuucuauac uaagucuacg uucccagacg    60
acucgcccga                                                          70

<210> SEQ ID NO 87
<211> LENGTH: 72
<212> TYPE: RNA
<213> ORGANISM: Artificial Sequence
<220> FEATURE:
<223> OTHER INFORMATION: Synthetic

<400> SEQUENCE: 87
gggaggacga ugcggaucag ccauguuuac gucacuccuu gucaauccuc aucggcagac    60
gaacucgccc ga                                                       72

<210> SEQ ID NO 88
<211> LENGTH: 40
<212> TYPE: DNA
<213> ORGANISM: Artificial Sequence
<220> FEATURE:
<223> OTHER INFORMATION: Synthetic

<400> SEQUENCE: 88
ggcaagctga ccctgaagtt cttttaggag tgacgtaaac                        40

<210> SEQ ID NO 89
<211> LENGTH: 32
<212> TYPE: DNA
<213> ORGANISM: Artificial Sequence
<220> FEATURE:
<223> OTHER INFORMATION: Synthetic

<400> SEQUENCE: 89
taatacgact cactataggg aggacgatgc gg                                32

<210> SEQ ID NO 90
<211> LENGTH: 21
<212> TYPE: RNA
<213> ORGANISM: Artificial Sequence
<220> FEATURE:
<223> OTHER INFORMATION: Synthetic

<400> SEQUENCE: 90
caagcugacc cugaaguucu u                                            21

<210> SEQ ID NO 91
<211> LENGTH: 30
<212> TYPE: DNA
<213> ORGANISM: Artificial Sequence
<220> FEATURE:
```

<223> OTHER INFORMATION: Synthetic

<400> SEQUENCE: 91
aaaggatcca tggctggtga tctttcagca                                        30

<210> SEQ ID NO 92
<211> LENGTH: 36
<212> TYPE: DNA
<213> ORGANISM: Artificial Sequence
<220> FEATURE:
<223> OTHER INFORMATION: Synthetic

<400> SEQUENCE: 92
ggactcgagt cattacactg aggtttcttc tgataa                                 36

<210> SEQ ID NO 93
<211> LENGTH: 47
<212> TYPE: DNA
<213> ORGANISM: Artificial Sequence
<220> FEATURE:
<223> OTHER INFORMATION: Synthetic

<400> SEQUENCE: 93
ttctcgaggt ggtggtggtg gtggtgcact gaggtttctt ctgataa                     47

<210> SEQ ID NO 94
<211> LENGTH: 47
<212> TYPE: DNA
<213> ORGANISM: Artificial Sequence
<220> FEATURE:
<223> OTHER INFORMATION: Synthetic

<400> SEQUENCE: 94
ttctcgaggt ggtggtggtg gtggtgcact gaggtttctt ctgataa                     47

<210> SEQ ID NO 95
<211> LENGTH: 83
<212> TYPE: DNA
<213> ORGANISM: Artificial Sequence
<220> FEATURE:
<223> OTHER INFORMATION: Synthetic

<400> SEQUENCE: 95
ttctcgaggt ggtggtggtg gtggtggtgg tggtggtggt ggtggtggtg gtggtggtgg       60
tgcactgagg tttcttctga taa                                               83

<210> SEQ ID NO 96
<211> LENGTH: 206
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(4)
<223> OTHER INFORMATION: optionally absent

<400> SEQUENCE: 96

Met Gly Ser Ser His His His His His His Ser Ser Gly Leu Val Pro
1               5                   10                  15

Arg Gly Ser His Met Ala Ser Met Thr Gly Gly Gln Gln Met Gly Arg
            20                  25                  30

Gly Ser Met Ala Gly Asp Leu Ser Ala Gly Phe Phe Met Glu Glu Leu
        35                  40                  45

```
Asn Thr Tyr Arg Gln Lys Gln Gly Val Val Leu Lys Tyr Gln Glu Leu
     50                  55                  60

Pro Asn Ser Gly Pro Pro His Asp Arg Arg Phe Thr Phe Gln Val Ile
 65                  70                  75                  80

Ile Asp Gly Arg Glu Phe Pro Glu Gly Glu Gly Arg Ser Lys Lys Glu
                 85                  90                  95

Ala Lys Asn Ala Ala Ala Lys Leu Ala Val Glu Ile Leu Asn Lys Glu
                100                 105                 110

Lys Lys Ala Val Ser Pro Leu Leu Leu Thr Thr Thr Asn Ser Ser Glu
            115                 120                 125

Gly Leu Ser Met Gly Asn Tyr Ile Gly Leu Ile Asn Arg Ile Ala Gln
130                 135                 140

Lys Lys Arg Leu Thr Val Asn Tyr Glu Gln Cys Ala Ser Gly Val His
145                 150                 155                 160

Gly Pro Glu Gly Phe His Tyr Lys Cys Lys Met Gly Gln Lys Glu Tyr
                165                 170                 175

Ser Ile Gly Thr Gly Ser Thr Lys Gln Glu Ala Lys Gln Leu Ala Ala
            180                 185                 190

Lys Leu Ala Tyr Leu Gln Ile Leu Ser Glu Glu Thr Ser Val
            195                 200                 205
```

<210> SEQ ID NO 97
<211> LENGTH: 220
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(4)
<223> OTHER INFORMATION: optionally absent

<400> SEQUENCE: 97

```
Met Gly Ser Ser His His His His His His Ser Ser Gly Leu Val Pro
 1               5                  10                  15

Arg Gly Ser His Met Ala Ser Met Thr Gly Gly Gln Gln Met Gly Arg
             20                  25                  30

Gly Ser Met Ala Gly Asp Leu Ser Ala Gly Phe Phe Met Glu Glu Leu
         35                  40                  45

Asn Thr Tyr Arg Gln Lys Gln Gly Val Val Leu Lys Tyr Gln Glu Leu
     50                  55                  60

Pro Asn Ser Gly Pro Pro His Asp Arg Arg Phe Thr Phe Gln Val Ile
 65                  70                  75                  80

Ile Asp Gly Arg Glu Phe Pro Glu Gly Glu Gly Arg Ser Lys Lys Glu
                 85                  90                  95

Ala Lys Asn Ala Ala Ala Lys Leu Ala Val Glu Ile Leu Asn Lys Glu
                100                 105                 110

Lys Lys Ala Val Ser Pro Leu Leu Leu Thr Thr Thr Asn Ser Ser Glu
            115                 120                 125

Gly Leu Ser Met Gly Asn Tyr Ile Gly Leu Ile Asn Arg Ile Ala Gln
130                 135                 140

Lys Lys Arg Leu Thr Val Asn Tyr Glu Gln Cys Ala Ser Gly Val His
145                 150                 155                 160

Gly Pro Glu Gly Phe His Tyr Lys Cys Lys Met Gly Gln Lys Glu Tyr
                165                 170                 175

Ser Ile Gly Thr Gly Ser Thr Lys Gln Glu Ala Lys Gln Leu Ala Ala
            180                 185                 190
```

```
Lys Leu Ala Tyr Leu Gln Ile Leu Ser Glu Glu Thr Ser Val His His
        195                 200                 205

His His His His Leu Glu His His His His
    210             215             220

<210> SEQ ID NO 98
<211> LENGTH: 226
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(4)
<223> OTHER INFORMATION: optionally absent

<400> SEQUENCE: 98

Met Gly Ser Ser His His His His Ser Ser Gly Leu Val Pro
1               5                   10                  15

Arg Gly Ser His Met Ala Ser Met Thr Gly Gly Gln Gln Met Gly Arg
            20                  25                  30

Gly Ser Met Ala Gly Asp Leu Ser Ala Gly Phe Phe Met Glu Glu Leu
        35                  40                  45

Asn Thr Tyr Arg Gln Lys Gln Gly Val Val Leu Lys Tyr Gln Glu Leu
    50                  55                  60

Pro Asn Ser Gly Pro Pro His Asp Arg Arg Phe Thr Phe Gln Val Ile
65                  70                  75                  80

Ile Asp Gly Arg Glu Phe Pro Glu Gly Glu Gly Arg Ser Lys Lys Glu
                85                  90                  95

Ala Lys Asn Ala Ala Ala Lys Leu Ala Val Glu Ile Leu Asn Lys Glu
            100                 105                 110

Lys Lys Ala Val Ser Pro Leu Leu Leu Thr Thr Thr Asn Ser Ser Glu
        115                 120                 125

Gly Leu Ser Met Gly Asn Tyr Ile Gly Leu Ile Asn Arg Ile Ala Gln
    130                 135                 140

Lys Lys Arg Leu Thr Val Asn Tyr Glu Gln Cys Ala Ser Gly Val His
145                 150                 155                 160

Gly Pro Glu Gly Phe His Tyr Lys Cys Lys Met Gly Gln Lys Glu Tyr
                165                 170                 175

Ser Ile Gly Thr Gly Ser Thr Lys Gln Glu Ala Lys Gln Leu Ala Ala
            180                 185                 190

Lys Leu Ala Tyr Leu Gln Ile Leu Ser Glu Glu Thr Ser Val His His
        195                 200                 205

His His His His His His His Leu Glu His His His His
    210                 215                 220

His His
225

<210> SEQ ID NO 99
<211> LENGTH: 232
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(4)
<223> OTHER INFORMATION: optionally absent

<400> SEQUENCE: 99
```

```
Met Gly Ser Ser His His His His His Ser Ser Gly Leu Val Pro
1               5                   10                  15

Arg Gly Ser His Met Ala Ser Met Thr Gly Gly Gln Gln Met Gly Arg
                20              25              30

Gly Ser Met Ala Gly Asp Leu Ser Ala Gly Phe Phe Met Glu Glu Leu
            35              40              45

Asn Thr Tyr Arg Gln Lys Gln Gly Val Val Leu Lys Tyr Gln Glu Leu
        50              55              60

Pro Asn Ser Gly Pro Pro His Asp Arg Arg Phe Thr Phe Gln Val Ile
65              70              75              80

Ile Asp Gly Arg Glu Phe Pro Glu Gly Glu Gly Arg Ser Lys Lys Glu
                85              90              95

Ala Lys Asn Ala Ala Ala Lys Leu Ala Val Glu Ile Leu Asn Lys Glu
            100             105             110

Lys Lys Ala Val Ser Pro Leu Leu Leu Thr Thr Thr Asn Ser Ser Glu
            115             120             125

Gly Leu Ser Met Gly Asn Tyr Ile Gly Leu Ile Asn Arg Ile Ala Gln
    130             135             140

Lys Lys Arg Leu Thr Val Asn Tyr Glu Gln Cys Ala Ser Gly Val His
145             150             155             160

Gly Pro Glu Gly Phe His Tyr Lys Cys Lys Met Gly Gln Lys Glu Tyr
                165             170             175

Ser Ile Gly Thr Gly Ser Thr Lys Gln Glu Ala Lys Gln Leu Ala Ala
            180             185             190

Lys Leu Ala Tyr Leu Gln Ile Leu Ser Glu Glu Thr Ser Val His His
            195             200             205

His His His His His His His His His His His His His His His His
        210             215             220

Leu Glu His His His His His
225             230
```

UNIVERSAL PROTEIN TAG FOR DOUBLE STRANDED NUCLEIC ACID DELIVERY

CROSS REFERENCE

This application is a U.S. national phase of International Application No. PCT/US 2014/061714, filed Oct. 22, 2014, which claims priority to U.S. Provisional Application No. 61/894,806, filed Oct. 23, 2013, the disclosures of which are hereby incorporated by reference in their entirety.

FEDERAL FUNDING STATEMENT

This invention was made with government support under grant nos. CA 140295 and CA 150301, awarded by the National Institutes of Health. The government has certain rights in the invention.

BACKGROUND siRNA is of considerable current interest because it can elicit potent, target-specific knockdown of virtually any mRNA, creating new opportunities for personalized medicine and for addressing a broad range of traditionally undruggable disease targets using small molecules. Similar to other antisense approaches, however, cell-specific delivery of siRNA technology in vivo still represents a major technical hurdle.

SUMMARY OF THE INVENTION

In a first aspect, the present invention provides a chimeric protein, comprising:

(a) one or more double stranded nucleic acid binding domains (dsNABD); and (b) one or more polyHis domains, where each polyHis domain comprises at least 3 consecutive histidine residues. In various embodiments, the one or more polyHis domains in total comprise at least 6, 12, 18, or more histidine residues. In another embodiment, only one polyHis domain is present. In a further embodiment, the one or more dsNABDs comprise one or more double stranded RNA binding domains (dsRBD). In exemplary embodiments, the one or more dsRBDs comprise an amino acid sequence selected from the group consisting of SEQ ID NOs:1-36 and 38-82.

In various other aspects, the invention provides recombinant nucleic acids encoding the chimeric protein of any embodiment or combination of embodiments of the invention, recombinant expression vectors comprising the recombinant nucleic acid of the invention, and recombinant host cells comprising the recombinant expression vectors of the invention.

In a further aspect, the invention provides compositions comprising (a) the chimeric protein of any embodiment or combination of embodiments of the invention and (b) a therapeutic comprising (i) a therapeutic double stranded nucleic acid; and (ii) a targeting ligand bound to the therapeutic double stranded nucleic acid, wherein the dsNABD of the chimeric protein is bound to the therapeutic double stranded nucleic acid. In one embodiment, the therapeutic double stranded nucleic acid comprises a therapeutic double stranded RNA, including but not limited to siRNA, small hairpin RNA (shRNA), or miRNA. In one embodiment, the therapeutic double stranded RNA comprises an siRNA. In a further embodiment, the targeting ligand is a single stranded aptamer, including but not limited an aptamer comprising a nucleic acid sequence selected from the group consisting of SEQ ID NOS:85-87.

In another aspect, the invention provides a use of the composition of any embodiment or combination of embodiments of the invention for treating a subject in need of treatment with the therapeutic double stranded nucleic acid. In a further aspect, the invention provides methods for reducing translation from a mRNA of interest, comprising contacting a cell or tissue comprising the mRNA with the composition of any embodiment or combination of embodiments of the invention for a time and under conditions to promote delivery of the siRNA into the cell or tissue to interfere with translation from the mRNA target of the siRNA.

DETAILED DESCRIPTION OF THE INVENTION

Figure 1:
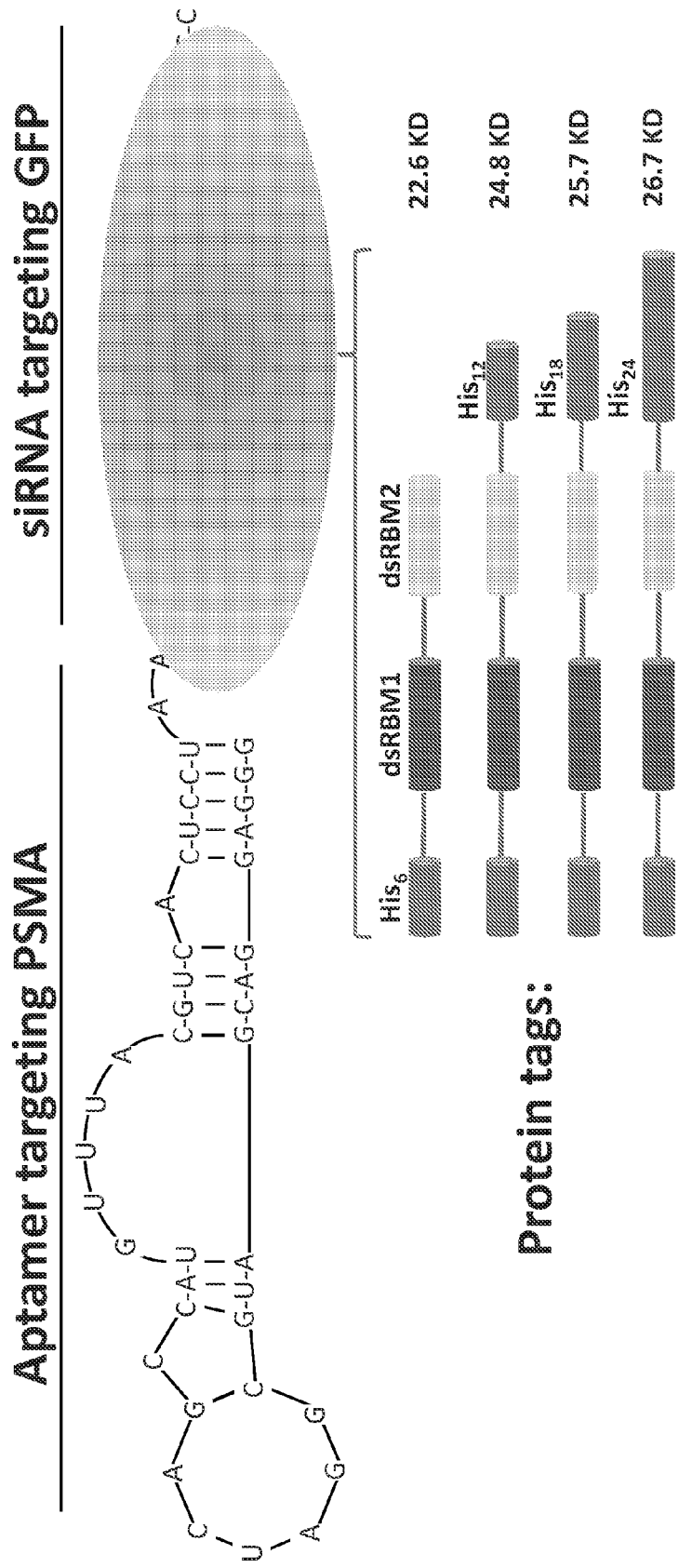
FIG. 1. Schematics of protein tags for siRNA-aptamer chimera delivery. Chimera composed of an aptamer block targeting PSMA and a siRNA block targeting GFP forms a hair-pin like structure. Protein tags specifically bound to the stem region (dsRNA) of the chimera complements it with endosomal escape capability. Protein tags with varying lengths of polyhistidines, as shown in the domain architectures, are engineered to achieve balanced endosomal escape and RNA binding functionalities.
Figure 2:
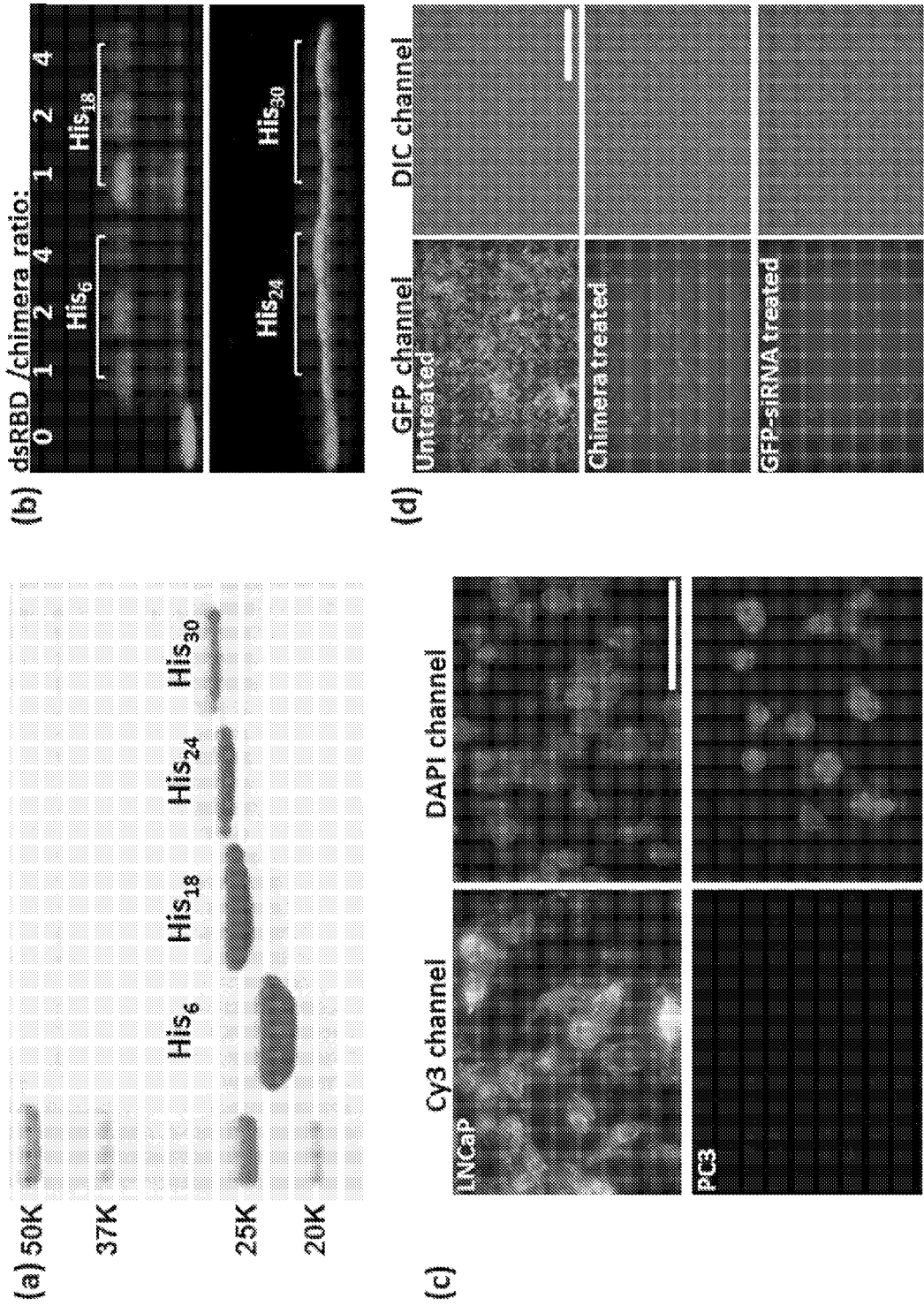
FIG. 2. Characterization of protein tags with varying lengths of polyhistidine and the siRNA-aptamer chimera. (a) SDS-PAGE analysis of protein tags composed of a dsRBD binding domain and polyhistidines at the two termini (total number of His: 6, 18, 24, and 30), in reference to protein ladder shown to the left. Motility patterns of the four protein tags are in agreement with their calculated molecular weights of 22.6 kDa ($His_6$), 24.8 kDa ($His_{18}$), 25.7 kDa ($His_{24}$), and 26.7 kDa ($His_{30}$). (b) Characterization of dsRNA binding capability of the four protein tags with agarose gel electrophoresis. Chimera labeled with fluorophore (FAM) was incubated with the protein tags at protein/chimera molar ratios of 1, 2, or 4 for 1 h at 4° C. The dsRNA binding capability of dsRBD-$His_{18}$ is well preserved compared to the original dsRBD-$His_6$, whereas dsRBD-$His_{24}$ and dsRBD-$His_{30}$ completely lose dsRNA binding activity. (c) Evaluation of targeting specificity of the aptamer block in chimera. PSMA-positive LNCaP cells and PSMA-negative PC3 cells are treated with complex of Cy3-labeled chimera and dsRBD-$His_{18}$ for 12 h. Fluorescence microscopy reveals selective binding of the complex to LNCaP cells, but not PC3 cells. Scale bar: 50 μm. (d) Evaluation of silencing functionality of the siRNA block. The chimera and conventional siRNA targeting GFP (positive control) are transfected into GFP-expressing C4-2 prostate cancer cells using Lipofectamine. The silencing effect of the chimera is indistinguishable with the positive control. Scale bar: 250 μm.
Figure 3:
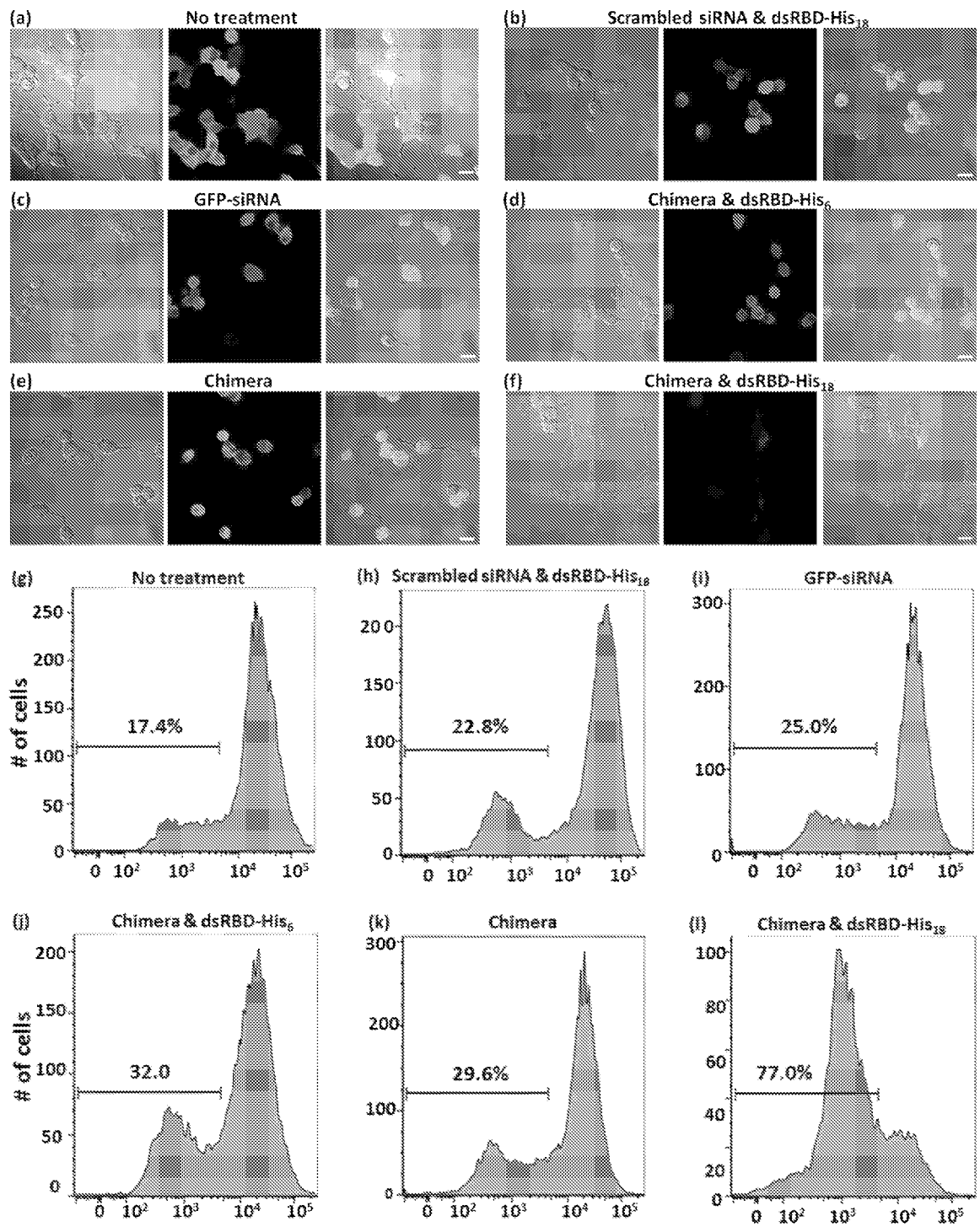
FIG. 3. Assessment of gene knockdown with confocal microscopy and flow cytometry. GFP expressing C4-2 cells are treated with chimera-dsRBD-$His_{18}$ complex and five controls, and the silencing effect is assessed with confocal microscopy (a-f) and quantified with flow cytometry (g-l). For confocal imaging, the panels from left to right are DIC, fluorescence, and merged images. In contrast to the control conditions (a, g) no treatment, (b, h) scrambled siRNA with dsRBD-$His_{18}$, (c, i) siRNA against GFP only, (d, j) chimera complexed with dsRBD-$His_6$, (e, k) chimera only (absence of transfection agents), the experimental group of chimera complexed with dsRBD-$His_{18}$ (f, l) shows significantly higher GFP knockdown. Scale bar as shown in (a) is consistent in the microscopy images, 20 μm.

All references cited are herein incorporated by reference in their entirety. As used herein, the singular forms "a", "an" and "the" include plural referents unless the context clearly dictates otherwise. "And" as used herein is interchangeably used with "or" unless expressly stated otherwise.

All embodiments of any aspect of the invention can be used in combination, unless the context clearly dictates otherwise.

As used herein, "about" means plus or minus 5% of the recited measurement.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above." and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

In a first aspect, the present invention provides chimeric proteins, comprising or consisting of:

(a) one or more double stranded nucleic acid binding domains (dsNABD); and (b) one or more polyHis domains, where each polyHis domain comprises at least 3 consecutive histidine residues.

The chimeric protein is one which is engineered to possess the one or more dsNABDs and the one or more polyHis domains (i.e.: does not encompass any naturally occurring protein). The inventors have surprisingly discovered that the chimeric proteins of the present invention provide a universal delivery vehicle for therapeutic double stranded nucleic acids that is capable of endosomal escape, and thus significantly improved efficacy of the therapeutic nucleic acid.

As used herein, a "polyHis" domain is a sequence of consecutive/contiguous His residues totaling at least 3. The one or more polyHis domains can be any suitable number of such domains that can be used to promote endosomal escape but no interfere with protein folding. In various embodiments, the chimeric protein may comprise 1, 2, 3, 4, 5, 6, 7, 8, 9, 10, or more polyHis domains. In various further embodiments, the polyHis domains may comprise 3, 6, 9, 12, 15, 18, 20, 23, or more His residues in total.

In various embodiments, the one or more polyHis domains may be present at the N-terminus, the C-terminus, or both the N-terminus and the C-terminus of the chimeric protein. In other embodiments, one or more polyHis domains may be present between two (or more) dsNABD, particularly in embodiments in which the chimeric protein includes linker amino acid sequences between multiple dsNABDs.

As will be understood by those of skill in the art, the chimeric proteins may comprise amino acid residues/domains in addition to the polyHis domain and the dsNABD; such additional domains may include purification tags, detectable tags, linker domains, etc. In one embodiment, the chimeric protein may comprise a linker domain of any suitable length between an dsNABD and a polyHis domain; in this embodiment, the number of polyHis domains may be increased, as the linker can limit the effect of the polyHis domains on folding of the dsNABDs. In another embodiment, the chimeric protein may comprise a linker domain of any suitable length between two dsNABDs.

As used herein, a dsNABD is a protein domain that binds to double stranded nucleic acid, including but not limited to double stranded DNA, RNA, or modified nucleic acids. In one embodiment, the dsNABD binds to double stranded RNA (dsRBD); in another embodiment, the dsNABD binds to double stranded DNA (dsDBD), including but not limited to zinc finger, leucine zipper, and helix-turn-helix domains. The double stranded nucleic acid may be any such ds nucleic acid that is to be delivered intracellularly. Non-limiting examples of such double stranded RNAs are small interfering RNAs (siRNAs), small hairpin RNAs (shRNAs), and micro-RNAs (miRNAs).

As will be understood by those of skill in the art, any suitable dsNABD can be used that binds appropriately to a given double stranded nucleic acid to be delivered. A wide variety of proteins containing dsRBDs are known, including but not limited to human protein kinase R (hPKR), DICER, Staufen, adenosine demainase acting on RNA (ADAR), spermatid perinuclear RNA binding protein, and a variety of other proteins as shown below in Tables 1and 2 below. These proteins typically share an evolutionarily-conserved dsRNA binding domain of about 65-68 amino acids. See, for example, Masliah et al., Cell. Mol. Life Sci. (2013) 70:1875-1895; Lupold et al, [Cancer Research 62, 4029-4033, Jul. 15, 2002]; and Nanduri et al., The EMBO Journal Vol. 17 No. 18 pp. 5458-5465, 1998. In one embodiment, the dsRBD comprises or consists of the amino acid sequence of SEQ ID NO:29 (consensus sequence of the evolutionarily-conserved dsRNA binding domain). In another embodiment, the dsRBD comprises or consists of the amino acid sequence of any one of SEQ ID NOS:4-28 and 30-36, and 38-82.

TABLE 1

DRBPs

| Species | | Accession number | DRBDs |
|---|---|---|---|
| FLJ20399 | Human | NP_060273 | 370-433 (SEQ ID NO: 30) |
| | Mouse | BAB26260 | 370-433 (SEQ ID NO: 31) |
| CG1434 | Drosophila | AAF48360 | 382-444 (SEQ ID NO: 32) |
| | A. gambiae (mosquito) | EAA12065 | 423-484 (SEQ ID NO: 33) |
| | C. elegans | CAA21662 | 360-423 (SEQ ID NO: 34) |
| | Human | XP_059208.4 | 101-169 (SEQ ID NO: 35) |
| | Mouse | XP_143416 | 45-113 (SEQ ID NO: 36) |
| CG13139 | Drosophila | AAF52926 | 28-96 (SEQ ID NO: 38) |
| | A. gambiae (partial) | EEA14824 | 44-112 (SEQ ID NO: 39) |
| DGCRK6 | Human | BAB83032 | 512-577, 620-684 (SEQ ID NO: 40) |
| | Mouse (partial) | XP_110167 | 42-107, 150-214 (SEQ ID NO: 41) |
| CG1800 | Drosophila | AAF57175 | 370-435, 486-544 (SEQ ID NO: 42) |
| | A. gambiae (partial) | EAA08039 | 300-365, 431-495 (SEQ ID NO: 43) |
| FLJ20036 | Human | AAH22270 | 461-536 (SEQ ID NO: 44) |
| | Mouse | XP_134159 | 445-520 (SEQ ID NO: 45) |
| MRP-L45 | Human | BAB14234 | 236-306 (SEQ ID NO: 46) |
| | Mouse | XP_129893 | 236-306 (SEQ ID NO: 47) |
| CG2109 | Drosophila | AAF52025 | 229-299 (SEQ ID NO: 48) |
| CG12493 | Drosophila | NP_647927 | 226-290 (SEQ ID NO: 49) |
| CG10630 | Drosophila | AAF50777 | 119-181, 253-316 (SEQ ID NO: 50) |
| CG17686 (DIP1) | Drosophila | AAD50502 | 172-233 (SEQ ID NO: 51) |
| | A. gambiae | EAA14308 | 180-245, 77-123 (SEQ ID NO: 52) |
| T22A3.5 | C. elegans | CAB03384 | 365-474 (SEQ ID NO: 53) |
| 25% RHA homology | O. sativa | AAL58955 | 1019-1078 (SEQ ID NO: 54) |
| | O. sativa | BAB55476 | 979-1041 (SEQ ID NO: 55) |
| | A. thaliana | NP_193898 | 871-938, 744-804 (SEQ ID NO: 56) |
| | A. thaliana | NP_195747 | 659-721 (SEQ ID NO: 57) |
| | D. disco | AAM43624 | 3-75 (SEQ ID NO: 58) |
| | O. sativa | BAB89847 | 2-44, 87-129, 170-222 (SEQ ID NO: 59) |
| | A. thaliana | AAL67059 | 5-71, 83-149 (SEQ ID NO: 60) |
| | A. thaliana | NP_198923 | 2-68, 88-154 (SEQ ID NO: 61) |
| | A. thaliana | NP_189329 | 2-44, 86-152 (SEQ ID NO: 62) |
| | A. thaliana | NP_565672 | 2-68, 88-132 (SEQ ID NO: 63) |
| | O. sativa | AAK21352 | 2-44, 88-132 (SEQ ID NO: 64) |
| | A. thaliana | NP_193824 | 14-74 (SEQ ID NO: 65) |

TABLE 2

Viral DRBPs

| | Accession number | Location of DRBDs |
|---|---|---|
| Vaccinia virus E3L | G42508 | 118-182 (SEQ ID NO: 66) |
| Sheeppox virus gene 30 | NP_659606 | 105-169 (SEQ ID NO: 67) |
| Lumpy skin disease virus (LSDV) LSDV034 | AAK84995 | 105-169 (SEQ ID NO: 68) |
| Orf virus IFN resistance gene OV20 | AAC08018 | 110-175 (SEQ ID NO: 69) |
| Reovirus ζ3 | P07939 | 234-297 (SEQ ID NO: 70) |
| Haemophilus influenzae | AAC21692 | 154-224 (SEQ ID NO: 71) |
| Paramecium bursaria clorella virus 1 (PBCV-1) gene A464R | AAC96831 | 202-267 (SEQ ID NO: 72) |
| Chilo iridescent virus (CIV) gene 340R | AAK82201 | 31-100 (SEQ ID NO: 73) |
| Coltivirus Vp8 | AAC72049 | 3-71 (SEQ ID NO: 74) |
| Coltivirus Vp12 | AAC72051 | 2-69 (SEQ ID NO: 75) |
| Drosophila C virus (DCV) | AAC58807 | 23-90 (SEQ ID NO: 76) |
| Replicase polyprotein Acyrthosiphon pisum virus P1 | AAC58718 | 2163-2227 (SEQ ID NO: 77) |
| Porcine group C rotavirus NSP3 | P27586 | 384-400 (SEQ ID NO: 78) |
| Bovine rotavirus | P34717 | 335-402 (SEQ ID NO: 79) |
| Human rotavirus | CAB52751 | 340-401 (SEQ ID NO: 80) |

As will be understood by those of skill in the art, the chimeric protein may contain more than one dsNABD; thus, in various embodiments, the dsNABD includes 1, 2, or more dsNABDS. When the construct includes more than one dsNABD, each dsNABD may be the same, or they may be different dsNABDs.

In one embodiment, the one or more dsNABDs comprise a dsRBD from human protein kinase R (hPKR). In one embodiment, the hPKR binding domain comprises or consists of the amino acid of SEQ ID NO:1 (hPKR RNA binding domain 1), SEQ ID NO:2 (hPKR RNA binding domain 2), SEQ ID NO:3 (consensus sequence of hPKR RNA binding domains 1 and 2). SEQ ID NO: 82 (hPKR RNA binding domains 1-2 plus linking sequences) and SEQ ID NO:81 (full length hPKR).

As used throughout the present application, the term "protein" is used in its broadest sense to refer to a sequence of subunit amino acids, whether naturally occurring or of synthetic origin. The proteins of the invention may comprise L-amino acids, D-amino acids (which are resistant to L-amino acid-specific protecases in vivo), or a combination of D- and L-amino acids. The proteins described herein may be chemically synthesized or recombinantly expressed. The proteins may be linked to other compounds to promote an increased half-life in vivo, such as by PEGylation, HESylation, PASylation, or glycosylation. Such linkage can be covalent or non-covalent as is understood by those of skill in the art. The proteins may be linked to any other suitable linkers, including but not limited to any linkers that can be used for purification or detection (such as FLAG or His tags).

In another aspect, the present invention provides isolated nucleic acids encoding the protein of any aspect or embodiment of the invention. The isolated nucleic acid sequence may comprise RNA or DNA. As used herein, "isolated nucleic acids" are those that have been removed from their normal surrounding nucleic acid sequences in the genome or in cDNA sequences. Such isolated nucleic acid sequences may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what nucleic acid sequences will encode the proteins of the invention.

In a further aspect, the present invention provides nucleic acid expression vectors comprising the isolated nucleic acid of any embodiment of the invention operatively linked to a suitable control sequence. "Recombinant expression vector" includes vectors that operatively link a nucleic acid coding region or gene to any control sequences capable of effecting expression of the gene product. "Control sequences" operably linked to the nucleic acid sequences of the invention are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type known in the art, including but not limited plasmid and viral-based expression vectors. The control sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The construction of expression vectors for use in transfecting prokaryotic cells is also well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; *Gene Transfer and Expression Protocols*, pp. 109-128, ed. E. J. Murray, The Humana Press Inc., Clifton, N.J.), and the Ambion 1998 Catalog (Ambion, Austin, Tex.). The expression vector must be replicable in the host organisms either as an episome or by integration into host chromosomal DNA. In a preferred embodiment, the expression vector comprises a plasmid. However, the invention is intended to include other expression vectors that serve equivalent functions, such as viral vectors.

In another aspect, the present invention provides recombinant host cells comprising the nucleic acid expression vectors of the invention. The host cells can be either prokaryotic or eukaryotic. The cells can be transiently or stably transfected or transduced. Such transfection and transduction of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, *Molecular Cloning: A Laboratory Manual* (Sambrook, et al., 1989, Cold Spring Harbor Laboratory Press; *Culture of Animal Cells: A Manual of Basic Technique*, 2$^{nd}$ Ed. (R.I. Freshney. 1987. Liss, Inc. New York, N.Y.). A method of producing a polypeptide according to the invention is an additional part of the invention. The method comprises the steps of (a) culturing a host according to this aspect of the invention under conditions conducive to the expression of the polypeptide, and (b) optionally, recovering the expressed polypeptide. The expressed polypeptide can be recovered from the cell free extract, cell pellet, or recovered from the culture medium. Methods to purify recombinantly expressed polypeptides are well known to the man skilled in the art.

In a further aspect, the present invention provides compositions comprising the chimeric protein of any embodiment or combination of embodiments of the present invention; and a therapeutic comprising (i) a therapeutic double stranded nucleic acid; and (ii) a targeting ligand bound to the therapeutic double stranded nucleic acid, wherein the dsNABD of the chimeric protein is bound to the therapeutic double stranded nucleic acid.

The inventors demonstrate in the examples that follow that compositions of the invention can be used for more efficient delivery of double stranded therapeutic nucleic acids to an intended target.

The protein chimera of the composition can be any embodiment or combination of embodiments as discussed herein. For example, the chimeric protein may comprise 1, 2, 3, 4, 5, 6, 7, 8, 9, 10, or more polyHis domains. In various further embodiments, the polyHis domains may comprise 3, 6, 9, 12, 15, 18, 20, 23, or more His residues in total. The chimeric proteins may comprise amino acid residues/domains in addition to the polyHis domain and the dsNABD; such additional domains may include purification tags, detectable tags, linker domains, etc. In one embodiment, the chimeric protein may comprise a linker domain of any suitable length between the dsNABD and the polyHis domain; in this embodiment, the number of polyHis domains may be increased, as the linker can limit the effect of the polyHis domains on folding of the dsNABDs. In one embodiment, the dsNABD binds to double stranded RNA (dsRBD); in another embodiment, the dsNABD binds to double stranded DNA (dsDBD). In various further embodiments, the one or more dsNABD comprises one or more domains selected from the group consisting of SEQ ID NOS: 1-36 and 38-82. In another embodiment, the dsNABD comprises a domain comprising the amino acid sequence of SEQ ID NO: 29. The chimeric protein may contain more than one dsNABD; thus, in various embodiments, the dsNABD includes 1, 2, or more dsNABDS. When the construct includes more than one dsNABD, each dsNABD may be the same, or they may be different dsNABDs. In one embodiment, the one or more dsNABDs comprise a dsRBD from human protein kinase R (hPKR). In various embodiments, the dsRBD from hPKR comprises or consists of any one or more of SEQ ID NOS:1-3 and 82.

The composition further comprises a therapeutic comprising (i) a therapeutic double stranded nucleic acid, and (ii) a targeting ligand bound to the therapeutic double stranded nucleic acid, wherein the dsNABD of the chimeric protein is bound to the therapeutic double stranded nucleic acid (such as by base pairing). The therapeutic double stranded nucleic acid can comprise DNA (in which case the dsNABD is a dsDBD) or RNA (in which case the dsNABD is a dsRBD). Any suitable double stranded nucleic acid can be used that is appropriate for a given use of the composition.

In one embodiment, the therapeutic double stranded nucleic acid comprises or consists of a small interfering RNA (siRNA), a small hairpin RNA (shRNA), or a microRNA (miRNA). Any suitable siRNA, shRNA, or miRNA can be used that is appropriate for a therapeutic target of interest. As is known by those of skill in the art, large numbers of such sequences exist. For example, Ambion (now Life Technology) sells more than 200,000 siRNAs.

In embodiments where the therapeutic double stranded nucleic acid is an siRNA. Such siRNAs are well known in the art and are in various stages of clinical development. For example, see Kanasty et al., Nature Materials Volume 12:967-977 (2013); and Burnett and Rossi, Chemistry & Biology 19:60-71, Jan. 27, 2012.

The targeting ligand of the compositions of the invention can be any molecule that can be used to target the composition for delivery to a site of interest on or in a target cell/tissue. In various non-limiting embodiments, the targeting ligand may be a single stranded nucleic acid aptamer, an antibody, affibody, scFv molecule, or small molecule that selectively bind to a target cell/tissue. In all embodiments, the targeting ligand is attached to the double stranded therapeutic nucleic acid: in one embodiment, the targeting ligand is chemically linked to the double stranded therapeutic nucleic acid. In embodiments where the targeting ligand is an RNA aptamer and the double stranded therapeutic nucleic acid is an siRNA, shRNA, or miRNA, the two may be recombinantly expressed from an appropriate expression vector. Similarly, where the targeting ligand is a DNA aptamer and the double stranded therapeutic nucleic acid is double stranded DNA the two may be recombinantly expressed from an appropriate expression vector.

In one embodiment, the targeting ligand comprises a single stranded aptamer. As will be understood by those of skill in the art, a large number of aptamers have been developed to target different cells/tissues in vivo (see, for example, Front. Genet., 2 Nov. 2012|doi: 10.3389/fgene.2012.00234) and Burnett and Rossi, Chemistry & Biology 19:60-71, Jan. 27, 2012. In one embodiment, the aptamer may comprise or consist of a PSMA aptamer selected from the group consisting of SEQ ID NO:85, 86, and 87.

The compositions may further comprise (a) a lyoprotectant; (b) a surfactant; (c) a bulking agent; (d) a tonicity adjusting agent; (e) a stabilizer; (f) a preservative and/or (g) a buffer. In some embodiments, the buffer in the pharmaceutical composition is a Tris buffer, a histidine buffer, a phosphate buffer, a citrate buffer or an acetate buffer. The pharmaceutical composition may also include a lyoprotectant, e.g. sucrose, sorbitol or trehalose. In certain embodiments, the pharmaceutical composition includes a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the pharmaceutical composition includes a bulking agent, like glycine. In yet other embodiments, the pharmaceutical composition includes a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The pharmaceutical composition may also include a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the pharmaceutical composition additionally includes a stabilizer, e.g., a molecule which, when combined with a protein of interest substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride.

The therapeutic double stranded nucleic acid may be the sole active agent in the composition, or the composition may further comprise one or more other active agents suitable for an intended use.

The compositions described herein may further comprise a pharmaceutically acceptable carrier, diluent, or excipient. Such compositions are substantially free of non-pharmaceutically acceptable components, i.e., contain amounts of non-pharmaceutically acceptable components lower than permitted by US regulatory requirements at the time of filing this application. In some embodiments of this aspect, if the composition is dissolved or suspended in water, the composition further optionally comprises an additional pharmaceutically acceptable carrier, diluent, or excipient. In other embodiments, the compositions described herein are solid pharmaceutical compositions (e.g., tablet, capsules, etc.).

These compositions can be prepared in a manner well known in the pharmaceutical art, and can be administered by any suitable route. In a preferred embodiment, the pharmaceutical compositions and formulations are designed for oral, subcutaneous, or intravenuous administration. Conventional pharmaceutical carriers, aqueous, powder or oily bases, thickeners and the like may be necessary or desirable.

In a further aspect, the invention provides uses of the compositions of the invention to deliver the therapeutic double stranded nucleic acid to a subject in need of treatment that can be effected by the therapeutic double stranded nucleic acid. In embodiments where the therapeutic double stranded nucleic acid is an siRNA, the uses/methods are to interfere with translation from mRNA of the siRNA targets. Thus, for example, the methods may comprise contacting a cell or tissue comprising the target mRNA with the composition of any appropriate embodiment of the invention for a time and under conditions to promote delivery of the siRNA into the cell or tissue to interfere with translation from the mRNA target of the siRNA. As used herein, "contacting cell or tissue" can be in vitro or in vivo, including administering to a patient with a disorder to be treated by reducing translation from a target mRNA. Appropriate dosages of the compositions can be determined by an attending physician based on specifics of the composition, the disorder to be treated, and all other factors.

EXAMPLES siRNA-aptamer chimeras have emerged as one of the most promising approaches for targeted delivery of siRNA due to the modularity of their diblock RNA structure, relatively lower cost over other targeted delivery approaches, and, most importantly, the outstanding potential for clinical translation. However, additional challenges must be addressed for efficient RNA interference (RNAi), in particular, endosomal escape. Currently, vast majority of siRNA delivery vehicles are based on cationic materials, which form complexes with negatively charged siRNA. Unfortunately, these approaches complicate the formulations again by forming large complexes with heterogeneous sizes, unfavorable surface charges, colloidal instability, and poor targeting ligand orientation. Here, we report the development of a small and simple protein tag that complements the therapeutic and targeting functionalities of chimera with two functional domains: a dsRNA binding domain (dsRBD) for siRNA docking and a pH-dependent polyhistidine to disrupt endosomal membrane. The protein selectively tags along the siRNA block of individual chimera, rendering the overall size of the complex small, desirable for deep tissue penetration, and the aptamer block accessible for target recognition.

Introduction siRNA is of considerable current interest because it can elicit potent, target-specific knockdown of virtually any mRNA, creating new opportunities for personalized medicine and for addressing a broad range of traditionally undruggable disease targets using small molecules.[1-3] Similar to other antisense approaches, however, cell-specific delivery of siRNA technology in vivo still represents a major technical hurdle.[4] Therefore, it is of value to design a delivery system that is simple for potential regulatory approval and mass production, universal for all siRNA-aptamer chimera, neutral and siRNA-binding specific to ensure aptamer targeting, and small to avoid major alteration of chimera's biodistribution profile. A system simultaneously achieving these features could expedite clinically translation of the highly promising siRNA-aptamer chimera technology.

Here, we report the development of a small protein tag for efficient delivery of siRNA-aptamer chimeras. As shown in FIG. 1, the protein tag is composed of two functional domains: a dsRBD used as a siRNA docking module and a pH-dependent polyhistidine to help disrupt the endosomal membrane. The dsRBD is the N-terminal region (20 Kda) of human protein kinase that binds dsRNA in a sequence-independent fashion.[26, 27] Because aptamers are typically ssRNA with complex secondary structures, dsRBD does not bind with them (dsRBD only tolerates small bulges) and thus will selectively bind chimera through the siRNA end, leaving the aptamer end accessible.

To add endosomal escape functionality, a short histidine (His) oligomer is added to the C-terminus of the dsRBD. His molecules have a pKa value of approximately 6. At neutral pH (such as in circulation), they are mainly deprotonated (uncharged), which is desirable over positively charged counterparts due to reduced accumulation within the RES (reticuloendothelial system). Overall, this protein tag is equally small, simple, and biodegradable as siRNA-aptamer chimera, while perfectly complementing chimera's functionalities. When complexed together, they remain small in size, discrete and stable in solution, low positive charge for circulation, and simultaneously achieve therapeutic, targeting, and endosomal escaping capabilities.

Results

Expression and Characterization of dsBRD-$His_{18}$ Protein Tag. To add endosomal escape capability, a short polyhistidine peptide was added to dsRBD. The dsRBD domain comes from the first 172 amino acids of human protein kinase R (hPKR), and has two double-strand RNA binding motifs (dsRBM1 and dsRBM2) for cooperative and dsRNA-specific binding.[31] Because dsRBM1 towards the N terminal dominates the binding with dsRNA,[32] we introduced the histidine peptide towards the C terminal (FIG. 1) to minimize impact on dsRBD's biological activity. In theory, the endosomal escape capability should increase with longer His chain; on the other hand, long His chain could potentially interfere with dsRBD protein folding and binding. To achieve a balance, dsRBD with C-terminal Histidines of various lengths ($His_n$, n=0, 12, 18, and 24) were cloned into the PET28a(+) vector. BamH1 and Xho1 restriction enzyme sites were introduced to the 5'- and 3'-flanking region by PCR, respectively. Because all the genetic constructs contain $His_6$ at the N-terminal from the cloning vector (this N-terminal $His_6$ has been previously proved to have no impact on dsRBD binding),[26] the total numbers of His encoded by the final constructs are 6, 18, 24, and 30, respectively (sequences see Methods).

Post expression and purification, the resulted protein tags were analyzed with sodium dodecyl sulfate polyacrylamide gel electrophoresis (SDS-PAGE, FIG. 2*a*). The sizes of four protein tags show in excellent agreement with theoretical values (FIG. 1). To assess their dsRNA binding activity, siRNA-aptamer chimera labeled with fluorophore FAM were incubated with the protein tags and probed with gel electrophoresis (1% agarose). As shown in FIG. 2*b*, the dsRNA binding capability of dsRBD with $His_{12}$ at the C terminus (total $His_{18}$) is well preserved compared with dsRBD without a C-terminus histag insertion. The minimum RNA length for high affinity binding with dsRBD has been determined to be 16 base-pairs.[26] At the current RNA length, the siRNA segment and the adjacent short stem in the aptamer structure can bind with 1-2 copies of dsRBD.

More interestingly, the gel electrophoresis experiments also reveal that extending the C-terminal His by another 6 or 12 amino acids completely abolish dsRBD's binding activity. Therefore, for the following gene expression regulation studies we chose the dsRBD with a total of 18 His due to its balanced dsRNA binding and endosomal escape functionalities, in comparison with the original dsRBD with no C-terminus His as a control.

Design, Synthesis, and Characterization of siRNA-Aptamer Chimera. To evaluate the universal protein tag for siRNA-aptamer chimera, we first designed and made a chimera based on the protocols described by Dassie and coworkers, taking advantage of the shortened aptamer sequence for specific targeting of prostate specific antigen (PSMA) as well as the optimized siRNA strands with enhanced therapeutic potency.[15] PSMA has been identified as one of the most attractive cell surface markers for both prostate epithelial cells and neovascular endothelial cells.[36] Accumulation and retention of PSMA targeting probes at the site of tumor growth is the basis of radioimmunoscintigraphic scanning (e.g., ProstaScint scan) and targeted therapy for human prostate cancer metastasis. We replaced their siRNA sequence with a siRNA silencing GFP expression, because GFP is the best model for quantitative assessment of the silencing effect using optical imaging and flow cytometry.

The long ssRNA composed of PSMA aptamer and siRNA antisense strand (FIG. 1) was prepared by in vitro transcription with the presence of 2' fluoro-modified pyrimidies for improved resistance to ribonucleases. It has been shown previously that 2'-F modification is compatible with dsRBD binding unlike 2'-H or 2'-$OCH_3$ substitutes.[26, 37] The transcript was annealed to chemically synthesized siRNA sense strand. Before combining the chimera with our small protein tag, we first tested the activities of the chimera. To test the targeting function of the aptamer block, PSMA-positive LNCaP and PSMA-negative PC3 prostate tumor cells were incubated with dye-labeled chimera. As shown in FIG. 2*c*, the chimera selectively binds and enters LNCaP cells indicating targeting specificity. To test the silencing effect separately, the chimera was transfected into GFP-expressing C4-2 prostate tumor cells (a derivative of LNCaP) using conventional transfection agents, Lipofectamine. As shown in FIG. 2*d*, the silencing effect is indistinguishable with the positive control using siRNA only, proving that chimera can be enzymatically processed intracellularly to generate functional siRNA.

Targeting Delivery and Silencing in Cells. With the biological activities of our protein tag and siRNA-aptamer chimera separately characterized, we proceeded to evaluate the gene silencing effect of this simple yet functionally highly complementary protein tag in siRNA-aptamer chimera delivery. GFP-expressing C4-2 cell line was used as a model because of the advantages of fluorescence imaging techniques such as microscopy and quantitative flow cytometry. FIG. 3a-f shows confocal images of the C4-2 cells without treatment, treated with GFP-siRNA alone, chimera alone, a random sequenced siRNA with the protein tag ($His_{18}$), chimera with protein tag ($His_6$), and chimera with protein tag ($His_{18}$). Qualitatively, only the experimental treatment, chimera with protein tag ($His_{18}$), clearly shows GFP silencing, whereas none of the five control treatments leads to significant suppression of GFP expression.

Quantitative flow cytometry studies further confirm this result (FIGS. 3g-l). At the current gate value set for GFP fluorescence intensity, the original untreated cells showed a GFP-negative population of 17.4%. Treating the cells with a random sequenced siRNA with protein tag ($His_{18}$) shows virtually no change in this population (difference: 5.4% of total cell population, within error range) proving sequence-specific silencing of RNAi. For cells treated with GFP siRNA and chimera, the GFP negative cells only increase by 7.6% and 12.2% of the total cell population respectively. Even by increasing the chimera concentration by ten times (1 μM), the total GFP-negative cell population only increase by <20%, strongly suggesting the need of carrier materials. Direct comparison of the chimera tagged by dsRBD-$His_6$ and dsRBD-$His_{18}$ shows major difference in silencing efficiency, too (14.6% and 59.6% change). Taken together, these results clearly indicate that (1) chimera alone at concentration commonly used in RNAi experiments does not lead to effective silencing, and (2) $His_{18}$ is remarkably more effective than $His_6$ in endosomal destabilization since the dsRBD block is identical in structure and function. To put the silencing efficiency of dsRBD-$His_{18}$ in the context of those of conventional RNA delivery vehicles such as Lipofectamine, quantitative flow cytometry was also conducted. In agreement with the microscopy results, Lipofectamine reduces GFP-negative cells from the original 17.4% to 91.6% (74.2% change,), which is slightly more efficient than the protein tag. However, it is important to note that Lipofectamine delivers chimera into cells mainly via electrostatic interactions (positively charged Lipofectamine and negatively charged cell surface, non-targeted delivery), whereas our protein tag delivers chimera by cell type-specific molecular recognition (targeted delivery). It is also worth mentioning that the molar ratio of mixing chimera with protein tag is 1:2 because the siRNA block can bind up to 2 copies of dsRBD, although the second copy has very weak binding affinity. Indeed, changing the binding ratio to 1 or 4 does not affect the RNAi efficiency.

Figure 4:
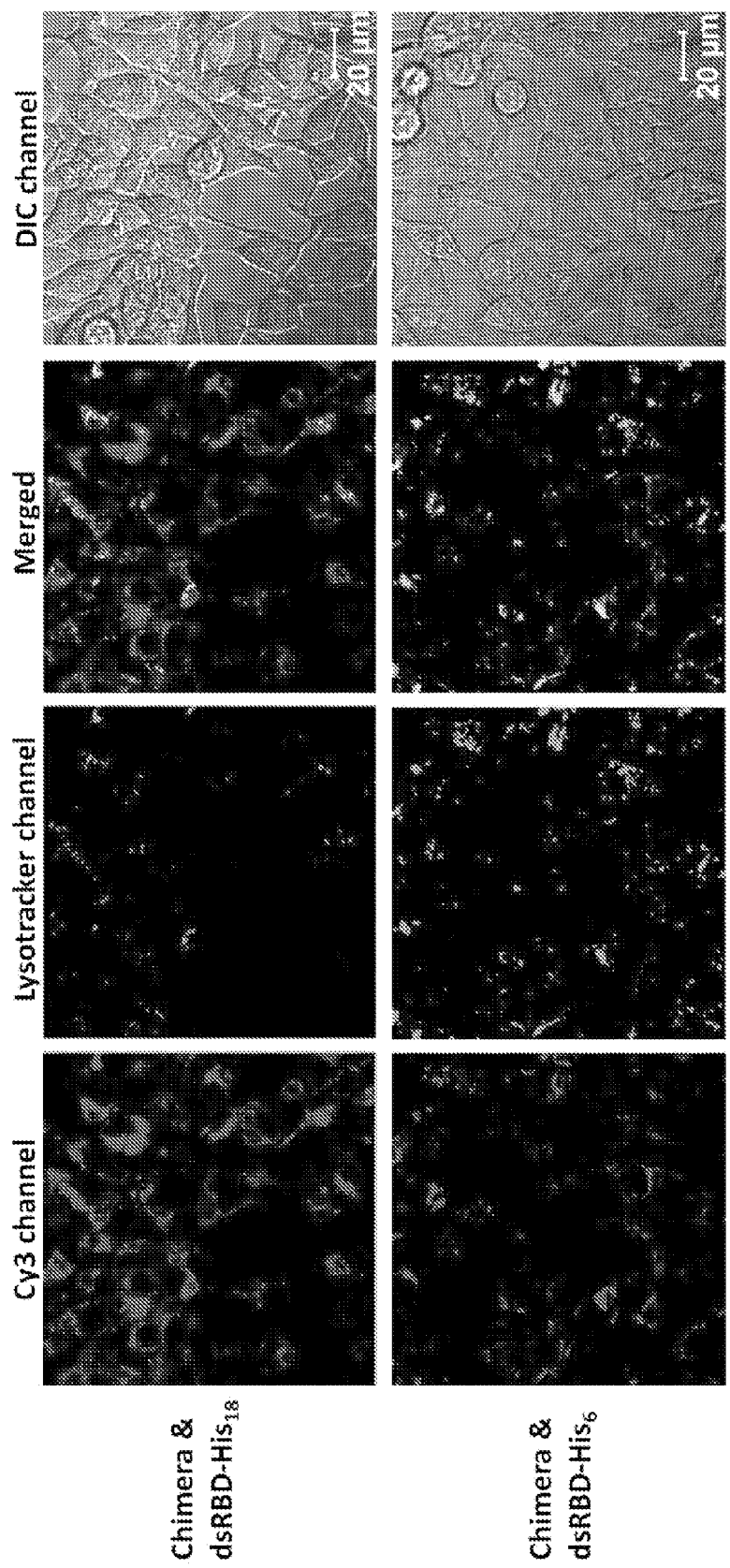
FIG. 4. Comparison of endosomal escape of protein tags, dsRBD-His$_6$ and dsRBD-His$_{18}$. Cy3-labeled chimera complexed with the two protein tags are added to LNCaP cells for 12 h, followed by Lysotracker Green staining for 4 h. Confocal laser scanning microscopy reveals homogeneous distribution of fluorescence of chimera tagged with dsRBD-His$_{18}$ and reduced endosome density compared to chimera complexed with dsRBD-His$_6$.

To further confirm the difference in endosomal escape capability between the two protein tags (dsRBD-$His_6$ and dsRBD-$His_{18}$), we performed a dual color imaging assay using non-fluorescence LNCaP cells. In this experiment, chimera was labeled with Cy3 and endosome/lysosome was marked with a LysoTracker (spectrally distinguishable green fluorescence). Direct contrast in chimera distribution and intracellular density of endosome/lysosome was observed between the two protein tags. As shown in FIG. 4, Cy3-labeled chimera evenly distributes inside cells when tagged by dsRBD-$His_{18}$, whereas dsRBD-$His_6$ treated cells show much higher density of endosomes and lysosomes and lower level of Cy3 fluorescence. This confocal imaging comparison directly explains the difference between the two protein tags in RNAi efficiency, and unambiguously demonstrates the superior endosome escape capability of dsRBD-$His_{18}$ over dsRBD-$His_6$.

Figure 5:
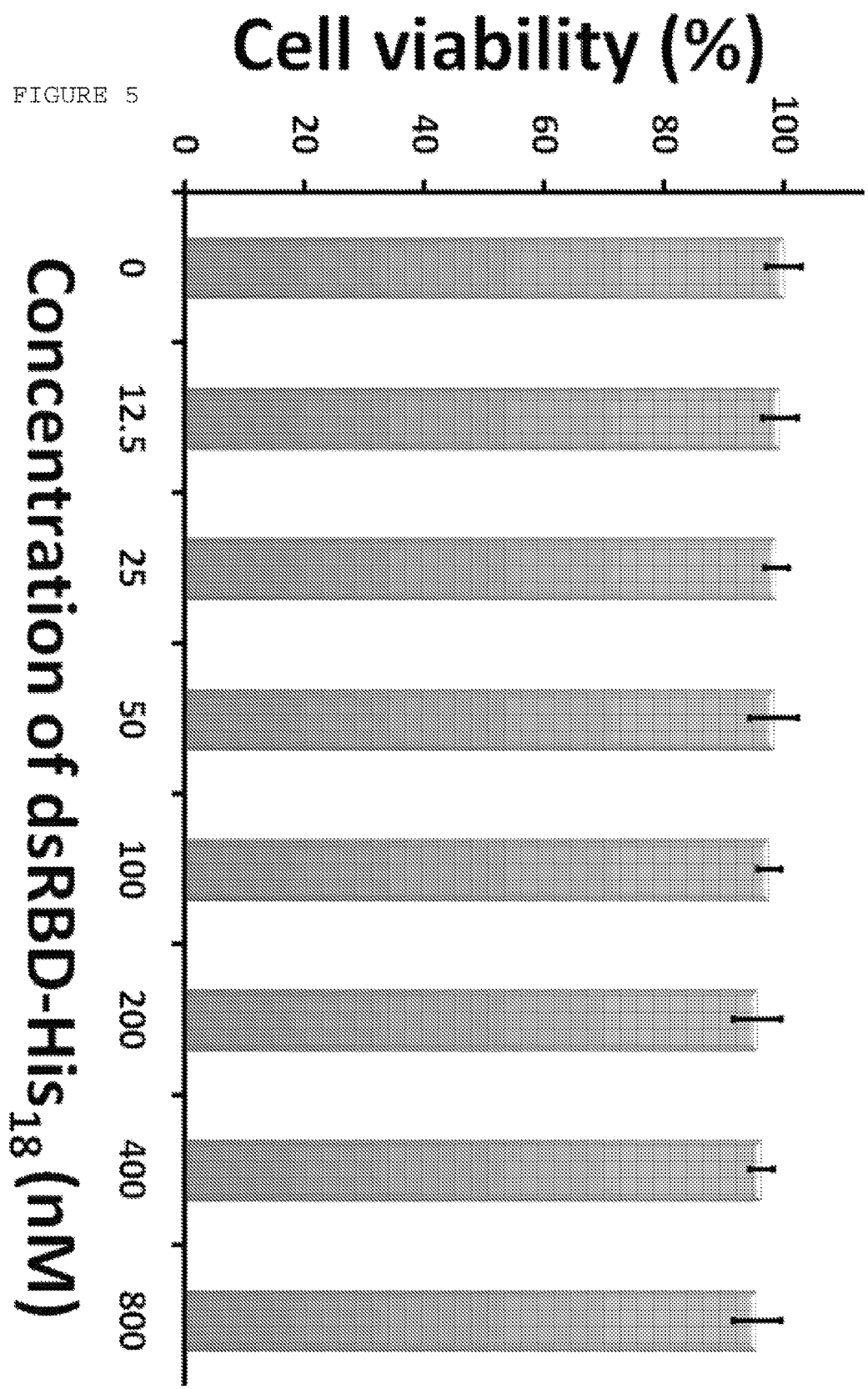
FIG. 5. Cytotoxicity evaluation of the dsRBD-His$_{18}$ protein tag. LNCaP cells are treated with the protein tag at various concentrations for 72 h, and the cell variability is quantified with CellTiter-Blue. Remarkably, dsRBD-His$_{18}$ protein tag exhibits no cytotoxicity throughout the measured concentration range up to 800 nM, which is four times as high as the concentration used in the siRNA delivery experiments. The data represents mean values from triplicate measurements.

Cytotoxicity. Lastly, we probed the cytotoxicity of the best performing protein tag dsRBD-$His_{18}$ using a standard cell viability assay (CellTiter-Blue®). The assay is based on the ability of living cells to convert a redox dye (resazurin) into a fluorescent end product (resorufin). Nonviable cells lose metabolic capacity and thus do not generate fluorescent signals. As illustrated in FIG. 5, virtually no toxicity was detected up to a concentration four times as high as the one used in the delivery work in reference to the untreated control. This is perhaps not too surprising due to the biocompatibility of dsRBD, a small protein of human origin. More importantly, for future in vivo applications, we envision that the small protein tag would have improved clearance capability compared with synthetic polymers and inorganic nanoparticles used for siRNA delivery.

Discussion siRNA-aptamer chimera is one of the most promising approaches for cell type-specific RNAi, owing to its low immunogenicity, ease of chemical synthesis and modification, small size, and the modularity of both the targeting aptamer block and the therapeutic siRNA segment. Almost all current targeted siRNA delivery formulations involve cationic nanocarriers such as polymers, inorganic nanoparticles, peptides, and proteins.[7, 19, 20, 27, 28, 38-44] Unfortunately, these conventional siRNA nanocarriers are unsuitable for chimera delivery, and, in fact, reverse the signature property of chimera, simple formulation for regulatory approval and clinical translation.[15, 16] This is because the charge induced complex formation is basically an aggregation process, which lacks control over aggregate size, shape, stoichiometry, chimera orientation, aptamer functionality, and reproducibility during scale-up production. In addition, the final complexes often carriers positive charges as well, which is unfavorable for systemic uses.[23]

Our protein tag does not rely on high positive charge to interact with RNA molecules. In fact, it only recognizes relatively long dsRNAs (>16 bp) such as the siRNA segment and the short stem region of the aptamer in our chimera molecule. Extensive biochemistry investigations have shown that for the current length of the chimera, maximum two copies of dsRBD can bind to it with differential affinity (the first copy binds much stronger than the second copy). The gene silencing experiments conducted here reflect this effect since mixing chimera with 1× or 2× protein tags does not affect the silencing efficiency. Considering the molecular weights of the chimera (28.8 kDa) and the protein tag (24.8 kDa), molecular weight of the final complex at 1:1 binding will become 53.6 kDa. Based on well-documented size effect for in vivo drug delivery,[49] this size is sufficiently large to reduce premature renal clearance while still small enough for deep tissue penetration. For example, by tagging siRNA-aptamer chimera with a 20 kDa PEG, its in vivo circulating half-life has been shown to increase from approximately 30 min to 30 hours;[15] whereas large nanoparticles (>30 nm) have been shown to be ineffective in tumor treatment except for some hyperpermeable tumors.[50]

In conclusion, to solve the endosome escape problem of the highly promising siRNA-aptamer chimera based therapy, we have designed a dual-block small protein by combining dsRBD and polyhistidine and identified the optimal length of polyhistidine. The resulting protein tag shares the simplicity feature of siRNA-aptamer chimera, yet offers exactly complementary functionalities. The dsRBD selectively binds to the siRNA block, leaving the targeting aptamer accessible. In terms of size, different from conventional cationic delivery vehicles, the dsRBD-His$_{18}$ tagged chimera remains discrete in solution rather than forming large aggregates. In terms of functionalities, chimera and dsRBD-His$_{18}$ are highly complementary to each other, and thus offer the complete set of features necessary for targeted siRNA delivery (e.g., targeting, therapeutic, siRNA protection, and endosomal escape). This platform is also universal, able to chaperone any chimera sequences for cell type-specific delivery. Largely based on natural proteins, dsRBD-His$_{18}$ is an excellent candidate for potential clinical translation because of its simple structure and biodegradability. Further development of this small protein tag with in vivo testing should raise exciting opportunities for siRNA clinical translation and personalized medicine.

Methods

Materials. Vendors for specific chemicals are listed below. In general, restriction enzymes were obtained from New England BioLabs, and cell culture products were purchased from Gibco/Invitrogen.

Chimera Composed of Aptamer Targeting PSMA and siRNA Targeting GFP. ssDNA of the PSMA aptamer (39 nucleotides, 5'-GGGAGGACGATGCGGATCAGCCAT-GTTTACGTCACTCCT-3')(SEQ ID NO: 85) was chemically synthesized by Integrated DNA Technologies (IDT) and used as the template to generate one strand of the siRNA-aptamer chimera. For amplification, PCR was performed with 3' primer containing the anti-sense strand of GFP siRNA (underlined) and 5' primer containing T7 RNA polymerase promoter site (bolded). The PCR primer sequences are:

```
3' primer:
                                       (SEQ ID NO: 88)
5'-GGCAAGCTGACCCTGAAGTTCTTTTAGGAGTGACGTAAAC-3'

5' primer:
                                       (SEQ ID NO: 89)
5'-TAATACGACTCACTATAGGGAGGACGATGCGG-3'
```

The 81 bp PCR product was put into T-A cloning pCR 2.1 vector (Invitrogen). After sequencing, positive plasmids were selected and used as the template for PCR. The resulting PCR product was separated with 2% agarose gel and recovered with QIAEX 11 Gel Extraction Kit (Qiagen). The purified PCR product was used as the template for in vitro transcription with MEGAscriptT7 Kit (Ambion) according to manufacturer's instruction. 2'fluoro-modified pyrimidines (TriLink, San Diego) were added to replace CTP and UTP. RNA molecules generated by the transcription reaction were annealed with the sense strand of GFP siRNA (chemically synthesized with or without 5'-Cy3 or FAM by IDT). The sequence is 5'-(Cy3 or FAM)-CAAGCUGACCCUGAAGUUCUU-3' (SEQ ID NO: 90). For annealing, the transcribed RNA and the synthetic siRNA sense strand were mixed at molar ratio 1:1 in duplex buffer (IDT) and incubated at 94° C. for 3 min followed by slow cooling to 25° C. in 1 hour. The final chimera was store at −80° C.

Construction of dsRBD with Varying Lengths of Polyhistidine. Full-length PKR gene (clone ID 8068981, BC_101475, *Homo sapiens*) was ordered from Open Biosystems. The DNA sequence for dsRBD is composed of the first 172 amino acids of PKR. To add polyhistidine of varying lengths to the C-terminus, four constructs were developed by PCR. 5' primer: 5'-AAA GGATCC ATG GCT GGT GAT CTT TCA GCA-3' (SEQ ID NO: 91), containing BamH1 site (underlined), was applied to all four constructs. The 3' primers containing Xho1 site (bolded) are:

```
His6:
                                       (SEQ ID NO: 92)
5'-GGACTCGAG TCATTACACTGAGGTTTCTTCTGATAA-3'

His18:
                                       (SEQ ID NO: 93)
5'-TTCTCGAG GTGGTGGTGGTGGTGGTGCACTGAGGTTTC
TTCTGATAA-3'

His24:
                                       (SEQ ID NO: 94)
5'-TTCTCGAG GTGGTGGTGGTGGTGGTGGTGGTGGTG
GTGGTGCACTGAGGTTTCTTCTGATAA-3'

His30:
                                       (SEQ ID NO: 95)
5'-TTCTCGAG GTGGTGGTGGTGGTGGTGGTGGTGGTG
GTGGTGGTGGTGGTGGTGGTGCACTGAGGTTTCTTCTGAT
AA-3'.
```

The constructs were cloned into PET28a (+) expression vector (Novagen). The constructs for dsRBD-His$_6$ and dsRBD-His$_{18}$ were obtained using full-length PKR gene (clone ID 8068981) as PCR template, and the dsRBD-His$_{24}$ and dsRBD-His$_{30}$ constructs were made by grafting additional histidines to the dsRBD-His$_{18}$ plasmid using PCR. The restriction enzyme sites for BamH1 and Xho1 were introduced in the PCR primers for cloning. dsRBD-His$_6$ construct was introduced with two stop codons (TAA and TGA) before the Xho1 site. For the other three constructs, the reading frames cover the His$_6$ sequence in the vector at the C-terminal end before the stop codon. The PCR products and PET28a (+) expression vector were digested with BamH1 and Xho1 enzymes. Ligation was performed with Quick Ligation Kit (BioLabs) for 5 min at room temperature. Ligates were transformed into *E. coli* BL21 (DE3) competent cells for expression. The plasmids were verified with DNA sequencing.

The sequences for the protein tags are

```
dsRBD-His6:
                                       (SEQ ID NO: 96)
(M)(G)(S)(S)HHHHHHSSGLVPRGSHMASMTGGQQMGRGSMAGD

LSAGFFMEELNTYRQKQGVVLKYQELPNSGPPHDRRFTFQVIIDGR

EFPEGEGRSKKEAKNAAAKLAVEILNKEKKAVSPLLLTTTNSSEGL

SMGNYIGLINRIAQKKRLTVNYEQCASGVHGPEGFHYKCKMGQKEY

SIGTGSTKQEAKQLAAKLAYLQILSEEFSV dsRBD-His18:
                                       (SEQ ID NO: 97)
(M)(G)(S)(S)HHHHHHSSGLVPRGSHMASMTGGQQMGRGSMAGD

LSAGFEMEELNTYRQKQGVVLKYQELPNSGPPHDRRFTFQVIIDGR

EFPEGEGRSKKEAKNAAAKLAVEILNKEKKAVSPLLLTTTNSSEGL

SMGNYIGLINRIAQKKRLTVNYEQCASGVHGPEGFHYKCKMGQKEY

SIGTGSTKQEAKQLAAKLAYLQILSEETSVHHHHHHLEHHHHHH
```

-continued dsRBD-His$_{24}$:
(SEQ ID NO: 98)
(M)(G)(S)(S)HHHHHHSSGLVPRGSHMASMTGGQQMGRGSMAGD

LSAGFFMEELNTYRQKQGVVLKYQELPNSGPPHDRRFTFQVIIDGR

EFPEGEGRSKKEAKNAAAKLAVEILNKEKKAVSPLLLTTTNSSEGL

SMGNYIGLINRIAQKKRLTVNYEQCASGVHGPEGFHYCKMGQKEY

SIGTGSTKQEAKQLAAKLAYLQILSEETSVHHHHHHHHHHHHLEHH

HHHH dsRBD-His$_{30}$:
(SEQ ID NO: 99)
(M)(G)(S)(S)HHHHHHSSGLVPRGSHMASMTGGQQMGRGSMAGD

LSAGFFMEELNTYRQKQGVVLKYQELPNSGPPHDRRFTFQVIIDGR

EFPEGEGRSKKEAKNAAAKLAVEILNKEKKAVSPLLLTTTNSSEGL

SMGNYIGLINRIAQKKRLTVNYEQCASGVHGPEGFHYCKMGQKEY

SIGTGSTKQEAKQLAAKLAYLQILSEETSVHHHHHHHHHHHHHHHH

HHLEHHHHHH

Single colonies were selected and grown at 37° C. for 12 h in Circlegrow medium containing 30 µg/ml kanamycin. Overnight cultures were diluted at 1:100 (v/v) into fresh medium and incubated at 37° C. until the OD$_{600}$ values reach 0.5-1.0. Expression was induced by addition of isopropyl-β-D-thiogalactopyranoside (IPTG, 1 mM), and cell growth was continued for another 4-5 hour at 30° C. Cells were harvested by centrifugation (Beckman JA-10 rotor) at 10,000 g for 10 min and stored at −20° C.

Cells were suspended in Bug-Buster Mix (Novagen) with 5 ml reagent per gram of wet cell paste. Bug Buster Mix was added with protease inhibitor EDTA-free cocktail (Pierce), 10% glycerol, and 1.0 mM THP (Novagen). The cell suspensions were incubated on a shaker platform for 30 min at room temperature. Insoluble cell debris was removed by centrifugation (Beckman TL 120) at 20,000×g for 20 min at 4° C. The soluble extracts were loaded onto affinity columns with Ni-charged His Bind Resin (Novagen). Following washing with binding buffer and washing buffer, the desired proteins were eluted with 6 volume elution buffer (Novagen). The eluted proteins were dialyzed with PBS containing 10% glycerol and 0.1% (v/v) β-mercaptoethanol for 24 hours.

Purified proteins were probed using 12% SDS-PAGE and stained with Coomassie Brilliant Blue G-250 (Bio-Rad). Protein concentrations were determined with the Bio-Rad Protein Assay with bovine serum albumin as the standard.

Functional Characterization of siRNA-Aptamer Chimera. To test the functionality of the siRNA block, the chimera described above and GFP siRNA control (Qiagen) at a final concentration of 50 nM were transfected into C4-2 prostate cancer cells stably expressing GFP using Lipofectamine RNAi MAX (Invitrogen) following the instructions provided by the manufacturer. To evaluate the targeting specificity of the aptamer block, PSMA-positive LNCaP cells and PSMA-negative PC3 cells were treated with complex of chimera and dsRBD-His$_{18}$ (chimera/protein tag molar ratio at 1:2, 100 nM chimera) in serum free medium for 2 hours, followed by incubation in complete medium for another 12 h. DAPI (30 nM) was added to stain cell nuclei. Fluorescent images were captured on an Olympus IX-71 inverted microscope equipped with 5 long-pass filters and a colored CCD camera.

Characterization of RNA Binding Capability of the Four Protein Tags. The binding capabilities of the four polyhistidine modified dsRBD proteins were evaluated by native agarose gel. The chimera was labeled with FAM at the 5' end of siRNA's sense strand (IDT). To prepare chimera/dsRBD complex, chimera (5 µM, 10 µl) was incubated with the protein tags at protein/chimera molar ratios of 1, 2, or 4 for 1 h at 4° C. Bound chimera and unbound chimera were quantified on 1% agarose gel using a Macro imaging system (Lightools Research, CA).

Evaluation of Endosomal Escape. PSMA-expressing LNCaP cells were seeded on 35 mm glass-bottom petri dishes (MatTeck Corp) at a density of 5×10$^4$ cells/well for 24 hours in RPMI 1640 supplemented with 10% FCS. Complexes of chimera labeled with Cy3 (IDT) and protein tags (His$_6$ and His$_{18}$) were added to LNCaP cells in serum-free medium for 2 hours, followed by incubation in complete medium for 12 hours. LysoTracker® Green DND-26 (80 nM, Invitrogen) was then added for 4 hours at 37° C. Images were captured on a confocal laser scanning microscope (LSM 510, Carl Zeiss, Germany).

Microscopy and Flow Cytometry Studies of Gene Knockdown Efficacy. C4-2 prostate cancer cells expressing GFP were seeded into 35 mM glass-bottom petri dishes for confocal imaging or 6-well plates for flow cytometry. Cells were treated with chimera & dsRBD-His$_{18}$ and compared with five control groups including no treatment, treated with GFP-siRNA alone, chimera alone, a random sequenced siRNA with the protein tag (His$_{18}$), and chimera with protein tag (His$_6$) for 2 h in serum free media and then incubated in complete media for 60 h. Confocal images were again obtained with LSM 510 confocal microscope equipped with argon (488 nm) and HeNe (543 nm) lasers; and quantitative flow cytometry investigation was done on a BD FACSCantoII flow cytometer.

Cytotoxicity Assay. LNCaP cells were seeded in 96-well plate at 4×10$^3$/well for 24 hours, and then treated with different concentrations of dsRBD-His$_{18}$ protein tag for 72 hours. CellTiter-Blue reagent (20 µl) was added into each well. After 4 h incubation at 37° C., cell viability was assessed by fluorescence intensity at 590 nm (excitation 570 nm) on a TECAN infinite M200 microplate reader.

REFERENCES

1. Dykxhoorn, D. M., Novina, C. D. & Sharp. P. A. Killing the messenger: short RNAs that silence gene expression. *Nat. Rev. Mol. Cell Biol.* 4, 457-467 (2003).
2. Hannon, G. J. RNA interference. *Nature* 418, 244-251 (2002).
3. Scherer. L. J. & Rossi, J. J. Approaches for the sequence-specific knockdown of mRNA. *Nat. Biotechnol.* 21, 1457-1465 (2003).
4. Whitehead, K. A., Langer, R. & Anderson, D. G. Knocking down barriers: advances in siRNA delivery. *Nat. Rev. Drug Discov.* 8, 129-138 (2009).
5. Chiu, Y. L., Ali, A., Chu, C. Y., Cao, H. & Rana, T. M. Visualizing a correlation between siRNA localization, cellular uptake, and RNAi in living cells. *Chem. Biol.* 11, 1165-1175 (2004).
6. Jeong. J. H., Mok, H., Oh. Y. K. & Park, T. G. siRNA conjugate delivery systems. *Bioconjug. Chem.* 20, 5-14 (2009).
7. Moschos, S. A. et al. Lung delivery studies using siRNA conjugated to TAT(48-60) and penetratin reveal peptide induced reduction in gene expression and induction of innate immunity. *Bioconjug. Chem.* 18, 1450-1459 (2007).
8. Nishina, K. et al. Efficient in vivo delivery of siRNA to the liver by conjugation of alpha-tocopherol. *Mol. Ther.* 16, 734-740 (2008).
9. Soutschek, J. et al. Therapeutic silencing of an endogenous gene by systemic administration of modified siRNAs. *Nature* 432, 173-178 (2004).
10. Wolfrum, C. et al. Mechanisms and optimization of in vivo delivery of lipophilic siRNAs. *Nat. Biotechnol.* 25, 1149-1157 (2007).
11. Bock, L. C., Griffin, L. C., Latham, J. A., Vermaas. E. H. & Toole. J. J. Selection of single-stranded-DNA molecules that bind and inhibit human thrombin. *Nature* 355, 564-566 (1992).
12. Ellington, A. D. & Szostak, J. W. In vitro selection of RNA molecules that bind specific ligands. *Nature* 346, 818-822 (1990).
13. Hermann, T. & Patel, D. J. Biochemistry—Adaptive recognition by nucleic acid aptamers. *Science* 287, 820-825 (2000).
14. Nimjee, S. M., Rusconi. C. P. & Sullenger, B. A. in *Annual Rev. Med,* 56, 555-583 (2005).
15. Dassie, J. P. et al. Systemic administration of optimized aptamer-siRNA chimeras promotes regression of PSMA-expressing tumors. *Nat. Biotechnol,* 27, 839-849 (2009).
16. McNamara, J. O., 2nd et al. Cell type-specific delivery of siRNAs with aptamer-siRNA chimeras. *Nat. Biotechnol.* 24, 1005-1015 (2006).
17. Levy-Nissenbaum, E., Radovic-Moreno, A. F., Wang, A. Z., Langer, R. & Farokhzad, O. C. Nanotechnology and aptamers: applications in drug delivery. *Trends Biotechnol.* 26, 442-449 (2008).
18. Derfus, A. M., Chen, A. A., Min, D. H., Ruoslahti, E. & Bhatia, S. N. Targeted quantum dot conjugates for siRNA delivery. *Bioconjug. Chem.* 18, 1391-1396 (2007).
19. Elbakry, A. et al. Layer-by-layer assembled gold nanoparticles for siRNA delivery. *Nano Lett.* 9, 2059-2064 (2009).
20. Medarova, Z., Pham, W., Farrar. C., Petkova, V. & Moore, A. In vivo imaging of siRNA delivery and silencing in tumors. *Nat. Med.* 13, 372-377 (2007).
21. Meng, H. et al. Engineered design of mesoporous silica nanoparticles to deliver doxorubicin and P-glycoprotein siRNA to overcome drug resistance in a cancer cell line. *ACS Nano* 4, 4539-4550.
22. Xia, T. et al. Polyethyleneimine coating enhances the cellular uptake of mesoporous silica nanoparticles and allows safe delivery of siRNA and DNA constructs. *ACS Nano* 3, 3273-3286 (2009).
23. Alexis, F., Pridgen, E., Molnar. L. K. & Farokhzad, O. C. Factors affecting the clearance and biodistribution of polymeric nanoparticles. *Mol. Pharm.* 5, 505-515 (2008).
24. Bagalkot, V. & Gao. X. siRNA-aptamer chimeras on nanoparticles: preserving targeting functionality for effective gene silencing. *ACS Nano* 5, 8131-8139 (2011).
25. Walter, J.-G., Kolˆkpinar, O. z., Friehs, K., Stahl, F. & Scheper, T. Systematic Investigation of Optimal Aptamer Immobilization for Proteinâ"Microarray Applications. *Anal. Chem.* 80, 7372-7378 (2008).
26. Bevilacqua, P. C. & Cech, T. R. Minor-groove recognition of double-stranded RNA by the double-stranded RNA-binding domain from the RNA-activated protein kinase PKR. *Biochemistry* 35, 9983-9994 (1996).
27. Eguchi, A. et al. Efficient siRNA delivery into primary cells by a peptide transduction domain-dsRNA binding domain fusion protein. *Nat. Biotechnol.* 27, 567-U110 (2009).
28. Pichon, C., Goncalves, C. & Midoux, P. Histidine-rich peptides and polymers for nucleic acids delivery. *Adv. Drug Del. Rev.* 53, 75-94 (2001).
29. Midoux, P., Pichon, C., Yaouanc, J. J. & Jaffres, P. A. Chemical vectors for gene delivery: a current review on polymers, peptides and lipids containing histidine or imidazole as nucleic acids carriers. *Br. J. Pharmacol.* 157, 166-178 (2009).
30. Behr, J. P. The proton sponge: A trick to enter cells the viruses did not exploit. *Chimia* 51, 34-36 (1997).
31. Nanduri, S., Carpick, B. W., Yang, Y. W., Williams, B. R. G. & Qin, J. Structure of the double-stranded RNA-binding domain of the protein kinase PKR reveals the molecular basis of its dsRNA-mediated activation. *Embo J.* 17, 5458-5465 (1998).
32. Green, S. R. & Mathews, M. B. 2 Rna-Binding Motifs in the Double-Stranded Rna-Activated Protein-Kinase, Dai. *Genes Dev.* 6, 2478-2490 (1992).
33. Kim, I., Liu, C. W. & Puglisi, J. D. Specific recognition of HIV TAR RNA by the dsRNA binding domains (dsRBD1-dsRBD2) of PKR. *J. Mol. Biol.* 358, 430-442 (2006).
34. Kim, J., Lee, S. H., Choe, J. & Park, T. G. Intracellular small interfering RNA delivery using genetically engineered double-stranded RNA binding protein domain. *J. Gene Med.* 11, 804-812 (2009).
35. Ko, Y. T., Kale, A., Harmer, W. C., Papahadjopoulos-Sternberg, B. & Torchilin, V. P. Self-assembling micelle-like nanoparticles based on phospholipid-polyethyleneimine conjugates for systemic gene delivery. *J. Controlled Release* 133, 132-138 (2009).
36. Chang, S. S., Reuter, V. E., Heston, W. D. W. & Gaudin, P. B. Metastatic renal cell carcinoma neovasculature expresses prostate-specific membrane antigen. *Urology* 57, 801-805 (2001).
37. Nallagatla, S. R. & Bevilacqua, P. C. Nucleoside modifications modulate activation of the protein kinase PKR in an RNA structure-specific manner. *RNA* 14, 1201-1213 (2008).
38. Davis, M. E. The first targeted delivery of siRNA in humans via a self-assembling, cyclodextrin polymer-based nanoparticle: from concept to clinic. *Mol. Pharm.* 6, 659-668 (2009).
39. Green, J. J. et al. Electrostatic Ligand Coatings of Nanoparticles Enable Ligand-Specific Gene Delivery to Human Primary Cells. *Nano Lett.* 7, 874-879 (2007).
40. Howard, K. A. et al. RNA interference in vitro and in vivo using a novel chitosan/siRNA nanoparticle system. *Mol. Ther.* 14, 476-484 (2006).
41. Liu. X. et al. The influence of polymeric properties on chitosan/siRNA nanoparticle formulation and gene silencing. *Biomaterials* 28, 1280-1288 (2007).
42. Qi, L. & Gao, X. Quantum dot-amphipol nanocomplex for intracellular delivery and real-time imaging of siRNA. *ACS Nano* 2, 1403-1410 (2008).
43. Qi, L. & Gao. X. Emerging application of quantum dots for drug delivery and therapy. *Exp. Opin. Drug Del.* 5, 263-267 (2008).
44. Probst, C. E., Zrazhevskiy, P., Bagalkot, V. & Gao, X. H. Quantum dots as a platform for nanoparticle drug delivery vehicle design. *Adv. Drug Del. Rev.* 65, 703-718 (2013).

45. Bitko, V., Musiyenko, A., Shulyayeva, O. & Barik, S. Inhibition of respiratory viruses by nasally administered siRNA. *Nat. Med.* 11, 50-55 (2005).
46. DeVincenzo, J. et al. Evaluation of the safety, tolerability and pharmacokinetics of ALN-RSVO 1, a novel RNAi antiviral therapeutic directed against respiratory syncytial virus (RSV). *Antiviral Res.* 77, 225-231 (2008).
47. Li, B. J. et al. Using siRNA in prophylactic and therapeutic regimens against SARS coronavirus in rhesus macaque. *Nat. Med.* 11, 944-951 (2005).
48. Reich, S. et al. Small interfering RNA (siRNA) targeting VEGF effectively inhibits ocular neovascularization in a mouse model. *Mol. Vision* 9, 210-216 (2003).
49. Longmire, M., Choyke, P. L. & Kobayashi, H. Clearance properties of nano-sized particles and molecules as imaging agents: considerations and caveats. *Nanomedicine* 3, 703-717 (2008).
50. CabralH et al. Accumulation of sub-100 nm polymeric micelles in poorly permeable tumours depends on size. *Nat. Nanotechnol.* 6, 815-823 (2011).

We claim:

1. A chimeric protein, comprising:
   (a) one or more double stranded ribonucleic acid binding domains (dsRBDs), wherein the one or more dsRBDs comprise the amino acid sequence selected from the group consisting of SEQ ID NOs: 2-36 and 38-80; and
   (b) one or more polyHis domains, wherein each polyHis domain comprises at least 6 consecutive histidine residues, and wherein the one or more polyHis domains in total consist of 18 histidine residues.

2. The chimeric protein of claim 1, wherein only one polyHis domain is present.

3. The chimeric protein of claim 1, wherein the one or more dsRBDs comprise two or more dsRBDs.

4. The chimeric protein of claim 1, wherein the one or more dsRBDs comprise the amino acid sequence of SEQ ID NO: 29.

5. The chimeric protein of claim 1, wherein the one or more dsRBDs comprise the amino acid sequence of SEQ ID NO: 1 and/or SEQ ID NO: 2.

6. The chimeric protein of claim 1, wherein the one or more dsRBDs comprises the amino acid sequence of SEQ ID NO: 81 or SEQ ID NO: 82.

7. A composition comprising:
   (a) the chimeric protein of claim 1; and
   (b) a therapeutic comprising (i) a therapeutic double stranded ribonucleic acid (RNA); and (ii) a targeting ligand bound to the therapeutic double stranded RNA, wherein the one or more dsRBDs of the chimeric protein are bound to the therapeutic double stranded RNA.

8. The composition of claim 7, wherein the therapeutic double stranded RNA comprises small interfering ribonucleic acid (siRNA), small hairpin ribonucleic acid (shRNA), or micro ribonucleic acid (miRNA).

9. The composition of claim 8, wherein the therapeutic double stranded RNA comprises an siRNA.

10. The composition of claim 7, wherein the targeting ligand is a single stranded aptamer.

11. The composition of claim 10, wherein the aptamer comprises a nucleic acid sequence selected from the group consisting of SEQ ID NOs: 85-87.

12. A method for reducing translation from a messenger RNA (mRNA) of interest, the method comprising contacting a cell or tissue comprising the mRNA with the composition of claim 9, wherein the composition promotes delivery of the siRNA into the cell or tissue to interfere with translation from the mRNA targeted by the siRNA.

* * * * *